US012805187B2

(12) United States Patent
Hsiao et al.

(10) Patent No.: US 12,805,187 B2
(45) Date of Patent: Nov. 17, 2026

(54) NEAR-INFRARED ORGANIC SMALL MOLECULE WITH VINYL GROUPS AND ACTIVE LAYER MATERIAL AND ORGANIC OPTOELECTRONIC DEVICE USING THE SAME

(71) Applicant: Raynergy Tek Incorporation, Hsinchu (TW)

(72) Inventors: Yu-Tang Hsiao, Hsinchu (TW); Chuang-Yi Liao, Hsinchu (TW); Yeu-Ru Lee, Hsinchu (TW)

(73) Assignee: RAYNERGY TEK INCORPORATION, Hsinchu (TW)

( * ) Notice: Subject to any disclaimer, the term of this patent is extended or adjusted under 35 U.S.C. 154(b) by 577 days.

(21) Appl. No.: 18/232,004

(22) Filed: Aug. 9, 2023

(65) Prior Publication Data

US 2024/0107879 A1 Mar. 28, 2024

Related U.S. Application Data

(60) Provisional application No. 63/398,361, filed on Aug. 16, 2022.

(51) Int. Cl.

| | |
|---|---|
| ***C07D 495/22*** | (2006.01) |
| ***C07D 513/22*** | (2006.01) |
| ***H10K 30/20*** | (2023.01) |
| ***H10K 30/30*** | (2023.01) |
| ***H10K 30/60*** | (2023.01) |
| ***H10K 85/10*** | (2023.01) |
| ***H10K 85/40*** | (2023.01) |
| ***H10K 85/60*** | (2023.01) |

(52) U.S. Cl.

CPC ......... *H10K 85/657* (2023.02); *C07D 513/22* (2013.01); *H10K 85/113* (2023.02); *H10K 85/151* (2023.02); *H10K 85/626* (2023.02); *H10K 30/30* (2023.02)

(58) Field of Classification Search

CPC ..... C07D 495/22; C07D 513/22; C07F 7/081; H10K 30/30; H10K 30/60; H10K 30/20; H10K 85/657; H10K 85/113; H10K 85/151; H10K 85/626; H10K 85/40; H10K 85/615; H10K 85/656; H10K 85/6576

See application file for complete search history.

(56) References Cited

U.S. PATENT DOCUMENTS 11,925,101 B2 * 3/2024 Li ........................ C08G 61/126
2025/0255180 A1 * 8/2025 Hsiao ..................... H10K 85/30

FOREIGN PATENT DOCUMENTS

CN 110283185 A 9/2019
CN 111978335 A * 11/2020 ........... C07D 495/22
CN 112552313 A 3/2021
CN 113372365 A * 9/2021 ........... C07D 513/22
CN 113571639 A 10/2021
CN 114181229 A 3/2022
TW 202128716 A 8/2021
TW 202140606 A 11/2021

OTHER PUBLICATIONS

English translation of claims of CN-111978335-A, https://translationportal.epo.org/emtp/translate/?ACTION=claims-retrieval&COUNTRY=CN&ENGINE=google&FORMAT=docdb&KIND=A&LOCALE=en_EP&NUMBER=111978335&OPS=ops.epo.org/3.2&SRCLANG=zh&TRGLANG=en, Retrieved on Apr. 15, 2026. (Year: 2026).*

English translation of description of CN-111978335-A, https://translationportal.epo.org/emtp/translate/?ACTION=description-retrieval&COUNTRY=CN&ENGINE=google&FORMAT=docdb&KIND=A&LOCALE=en_EP&NUMBER=111978335&OPS=ops.epo.org/3.2&SRCLANG=zh&TRGLANG=en, Retrieved on Apr. 15, 2026. (Year: 2026).*

(Continued)

*Primary Examiner* — Kamal A Saeed
*Assistant Examiner* — Sagar Patel
(74) *Attorney, Agent, or Firm* — WPAT, PC

(57) ABSTRACT

An organic optoelectronic device comprises a first electrode, an active layer and a second electrode. An active layer material of the active layer comprises a near-infrared organic small molecule with vinyl groups which includes a structure of formula I:

(Formula I)

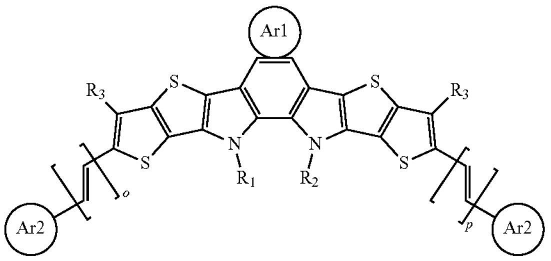

Wherein o and p are independently selected from any integer from 0 to 2, and o+p>0. Ar1 is an electron-withdrawing group with a unilateral fused ring structure. Ar2 is a monocyclic or polycyclic structure containing ketone and an electron-withdrawing group, and has a double bond to bond other groups. $R_1$ is different from $R_2$. The active layer material of the organic optoelectronic device comprises an organic small molecule with an asymmetric carbon chain, and has adjustable material solubility, arrangement and conductivity. The present invention also provides an active layer material comprising organic small molecules with asymmetric carbon chains and with symmetrical carbon chains independently, which improve production efficiency.

12 Claims, 5 Drawing Sheets

(56) References Cited

OTHER PUBLICATIONS

English translation of claims of CN-113372365-A, https://translationportal.epo.org/emtp/translate/?ACTION=claims-retrieval&COUNTRY=CN&ENGINE=google&FORMAT=docdb&KIND=A&LOCALE=en_EP&NUMBER=113372365&OPS=ops.epo.org/3.2&SRCLANG=zh&TRGLANG=en, Retrieved on Apr. 15, 2026. (Year: 2026).*

English translation of description of CN-113372365-A, https://translationportal.epo.org/emtp/translate/?ACTION=description-retrieval&COUNTRY=CN&ENGINE=google&FORMAT=docdb&KIND=A&LOCALE=en_EP&NUMBER=113372365&OPS=ops.epo.org/3.2&SRCLANG=zh&TRGLANG=en, Retrieved on Apr. 15, 2026. (Year: 2026).*

Taiwan Intellectual Property Office office action of the contracting TW application OA dated on Sep. 12, 2024.

Taiwan Intellectual Property Office NOA dated on Nov. 20, 2024.

China National Intellectual Property Administration Office OA dated on Sep. 6, 2025.

* cited by examiner

NEAR-INFRARED ORGANIC SMALL MOLECULE WITH VINYL GROUPS AND ACTIVE LAYER MATERIAL AND ORGANIC OPTOELECTRONIC DEVICE USING THE SAME

The present application is based on, and claims priority from, America provisional patent application number U.S. 63/398,361, filed on 2022 Aug. 16, the disclosure of which is hereby incorporated by reference herein in its entirety.

BACKGROUND OF THE INVENTION

Field of the Invention

The present invention relates to an organic small molecule, and more particularly, relates to a near-infrared organic small molecule with vinyl groups and an active layer material and an organic optoelectronic device using the same.

Description of the Prior Art

Compared with traditional inorganic optoelectronic devices, organic optoelectronic devices have a wide absorption wavelength range, high absorption coefficient and adjustable structure, and their light absorption range, energy level and solubility can be adjusted according to the target requirements. In addition, organic materials have the advantages of low cost, flexibility, low toxicity and large-area production of devices, so that organic optoelectronic devices have good competitiveness in various fields, such as organic field effect transistors (OFETs), organic light emitting diodes (OLEDs), organic photovoltaics (OPVs) and organic photodetectors (OPDs).

The organic optoelectronic device of the present invention takes the organic photodetectors as the key target. Organic photodetectors will have different material requirements according to different applications, and the application requirements for invisible region will be greatly increased. In the foreseeable future, the demand for invisible region applications will be increased significantly, for example, biometric technologies, such as vein scanners, iris sensors, and facial recognition. The physiological vital sign monitoring technology of pulse oximetry measurement, whose demand has increased due to the COVID-19 epidemic, and machine vision applications like LiDAR and time of flight sensors that are currently required by self-driving cars. Therefore, how to provide an organic photodetector with high performance and low cost in the absorption range of near infrared or shortwave infrared corresponding to the above applications is a very important issue at present. However, most of the materials in the literature having an absorption region only reach to the beginning of 900 nm, and the use of halogen-containing solvents in the device manufacturing process is not friendly to the environment. Therefore, the present invention hopes to develop a light-absorbing material covering 900~1000 nm, which has good device performance in non-halogen solvents.

Active layer materials play an important role in organic photodetectors and will directly affect device performance. The active layer material is divided into two parts: donor materials and acceptor materials. For the donor materials, the development of D-A conjugated polymers is the mainstream. The electron push-pull effect of electron-rich units and electron-deficient units in conjugated polymers can be used to control the energy levels and energy band gaps of polymers. The acceptor materials blended with the donor materials are usually fullerene derivatives with high conductivity, and its light absorption range is about 400~600 nm. However, the structure of fullerene derivatives is not easy to adjust, and their light absorption and energy levels are limited within a certain range, which limits the overall combination of the donor materials and the acceptor materials. With the development of the market, the demand for materials in the near-infrared region is gradually increasing. Even if the light absorption range of the conjugated polymer of the donor materials can be adjusted to the near-infrared region, it may not be able to have a good match due to the limitation of fullerene acceptor materials. Therefore, it is very important to develop non-fullerene acceptor materials to replace traditional fullerene acceptor materials in the breakthrough of active layer materials. The material development of the non-fullerene acceptor materials is mainly to form A-D-A ladder type molecules with electron-rich centers and electron-deficient units on both sides. D is usually a ladder type molecule composed of benzene and thiophene, and A is usually an indenone derivative. ITIC is a representative non-fullerene acceptor with an absorption range about 600~750 nm, and it also has good performance in organic photodetectors. In addition to the A-D-A ladder molecules, in 2019, the ladder type molecules published by Yang et. al with the A-D-A'-D-A structure, such as Y6, have a light absorption range of 600~900 nm, which further extends the light absorption spectrum of non-fullerene acceptors to near-infrared region. In photodetector applications, different photodetectors have different material requirements. In order to avoid sunlight interference, there are many gaps in the solar spectrum AM1.5. These gaps are just valuable for photodetector applications, but in the prior art, it is still insufficient to apply non-fullerene acceptors to photodetectors with a wavelength range about 900~1000 nm.

The purpose of the present invention is to provide a non-fullerene acceptor material that can absorb wavelengths in the range about 900~1000 nm, and use non-halogen solvents in the device manufacturing process to improve environmental friendliness, and maintain good performance and stability of organic photodetectors.

SUMMARY OF THE INVENTION

In view of this, the first category of the present invention is to provide a near-infrared organic small molecule with vinyl groups to break through the absorption capacity of the prior art in the near-infrared region. According to one embodiment of the present invention, the near-infrared organic small molecule with vinyl groups comprises a structure of formula I:

(formula I)

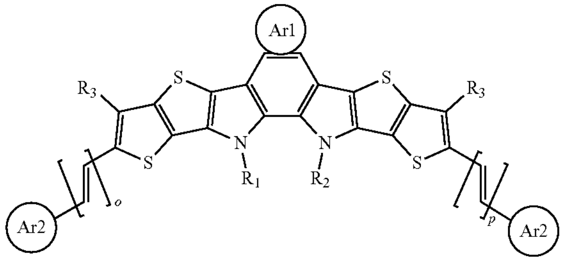

Wherein, o and p are independently selected from any integer from 0 to 2, and o+p>0. Ar1 is an electron-withdrawing group with a unilateral fused ring structure. Ar2 is a monocyclic or polycyclic structure containing ketone and an electron-withdrawing group, and has a double bond to bond other groups. $R_1$ is different from $R_2$, and $R_1$, $R_2$ and $R_3$ respectively are one of the following groups: C1~C30 alkyl, C1~C30 silyl, C1~C30 alkoxy, C1~C30 alkylthio, C1~C30 haloalkyl, C2~C30 ester, C1~C30 alkylaryl, C1~C30 alkylhetero aryl, C1~C30 silylaryl, C1~C30 s ilylhetero aryl, C1~C30 alkoxyaryl, C1~C30 alkoxyheteroaryl, C1~C30 alkylthioaryl, C1~C30 alkylthioheteroaryl, C1~C30 haloalkylaryl, C1~C30 haloalkylheteroaryl, C2~C30 ester aryl and C2~C30 ester heteroaryl.

Wherein, Ar1 further comprises a five-membered heterocyclic or a six-membered heterocyclic structure having at least one heteroatom, and the heteroatom is independently selected from at least one of S, N, O and Se.

Wherein, Ar1 is one of the following structures:

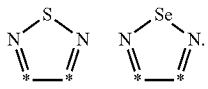

Wherein, Ar2 further comprises a fused ring structure of at least one of a five-membered ring and a six-membered ring, and the fused ring structure comprises at least one of C═O and cyano.

Wherein, Ar2 is one of the following structures:

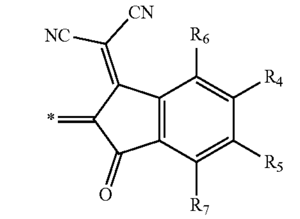

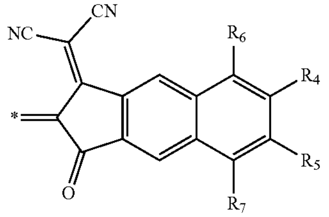

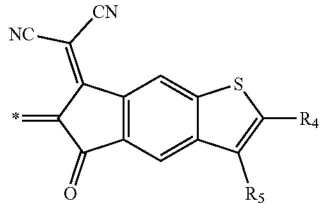

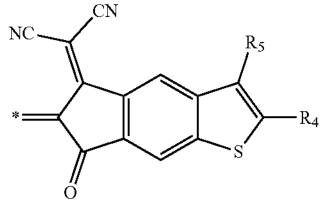

-continued

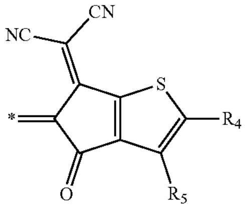

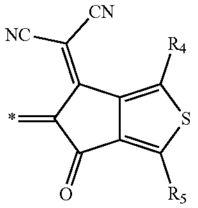

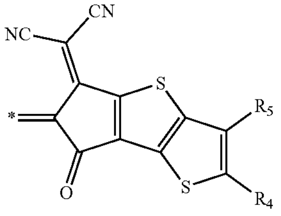

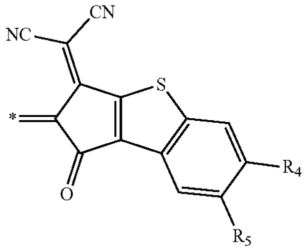

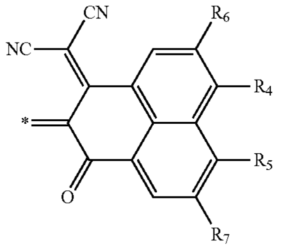

Wherein, $R_4$, $R_5$, $R_6$ and $R_7$ respectively are one of the following groups: C1~C30 alkyl, C1~C30 silyl, C1~C30 alkoxy, C1~C30 haloalkyl, halogen, cyano and hydrogen.

The second category of the present invention is to provide an active layer material which comprises an acceptor material and a donor material. The acceptor material comprises the near-infrared organic small molecule with vinyl groups aforementioned. The donor material comprises at least one organic conjugated polymer.

Wherein, the acceptor material further comprises at least one of the following structures:

(formula II)

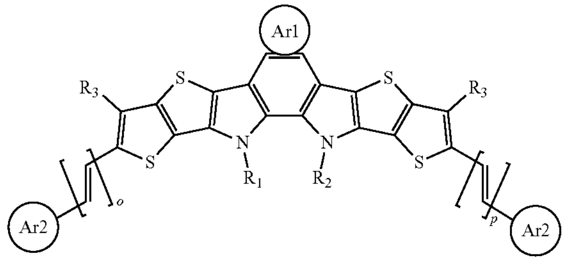

(formula III)

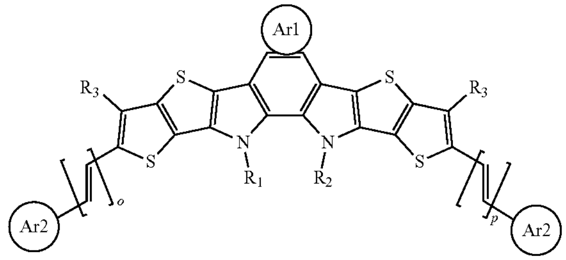

Wherein, o and p are independently selected from any integer from 0 to 2, and o+p>0. Ar1 is an electron-withdrawing group with a unilateral fused ring structure. Ar2 is a monocyclic or polycyclic structure containing ketone and an electron-withdrawing group, and has a double bond to bond other groups. $R_1$ is different from $R_2$, and $R_1$, $R_2$ and $R_3$ respectively are one of the following groups: C1~C30 alkyl, C1~C30 silyl, C1~C30 alkoxy, C1~C30 alkylthio, C1~C30 haloalkyl, C2~C30 ester, C1~C30 alkylaryl, C1~C30 alkylhetero aryl, C1~C30 silylaryl, C1~C30 s ilylhetero aryl, C1~C30 alkoxyaryl, C1~C30 alkoxyheteroaryl, C1~C30 alkylthioaryl, C1~C30 alkylthioheteroaryl, C1~C30 haloalkylaryl, C1~C30 haloalkylheteroaryl, C2~C30 ester aryl and C2~C30 ester heteroaryl.

Wherein, the acceptor material comprises the structures of formula I, formula II and formula III, wherein the molar ratios of the structures of formula I, formula II and formula III are a, b and c respectively, and $0<a\leq 1$, $0<b\leq 1$, $0<c\leq 1$, and $a+b+c=1$.

Wherein, the donor material further is one of the following structures:

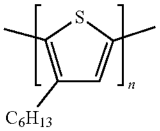

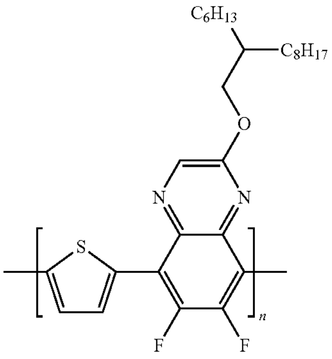

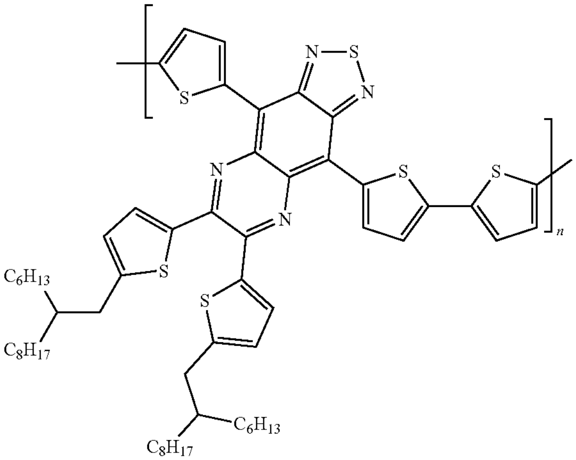

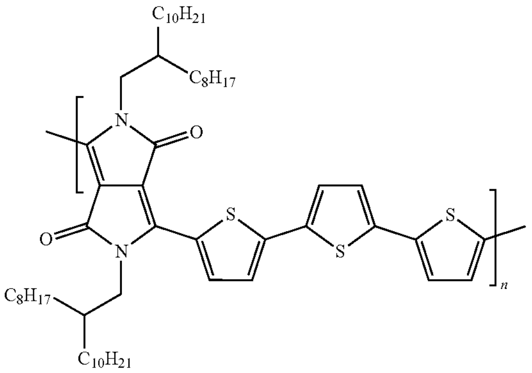

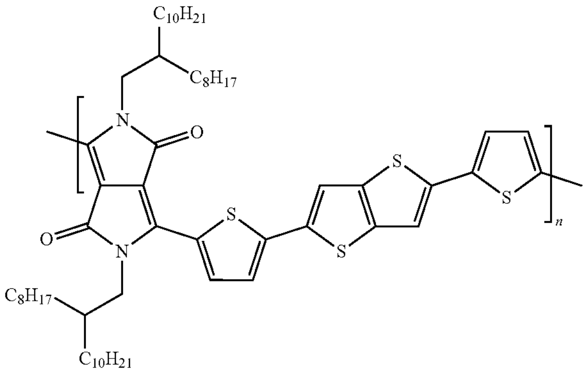

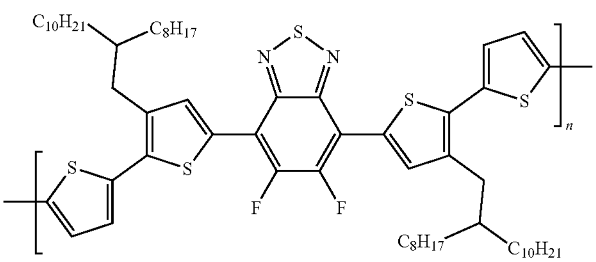

-continued
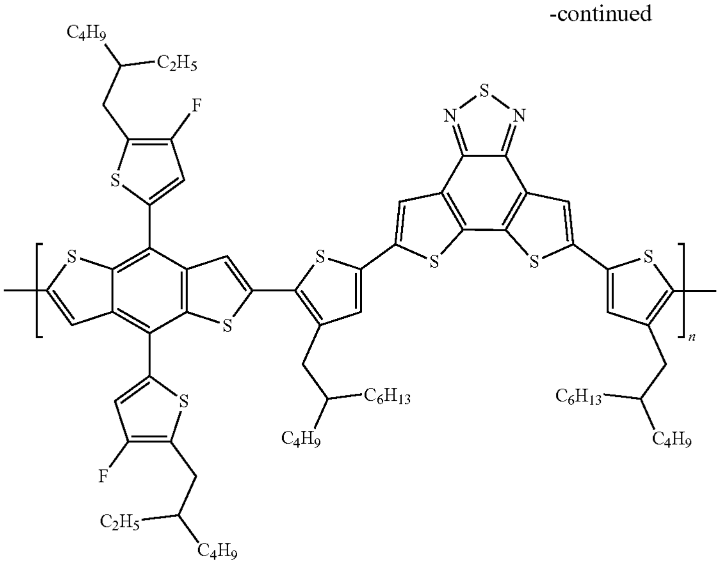
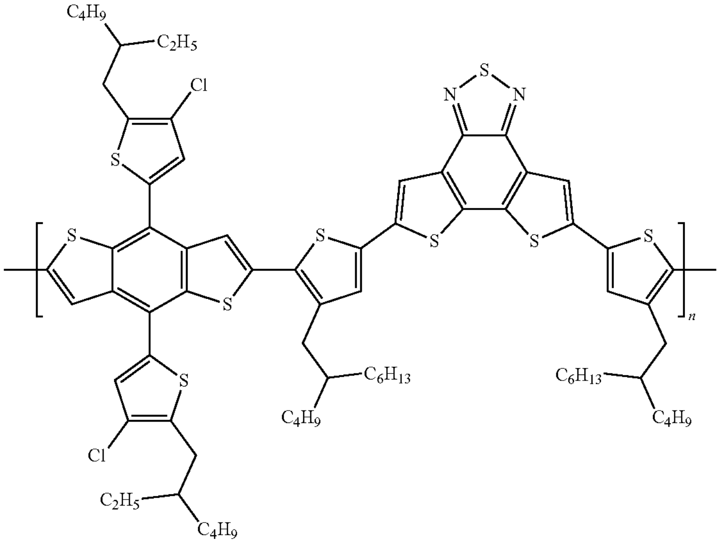
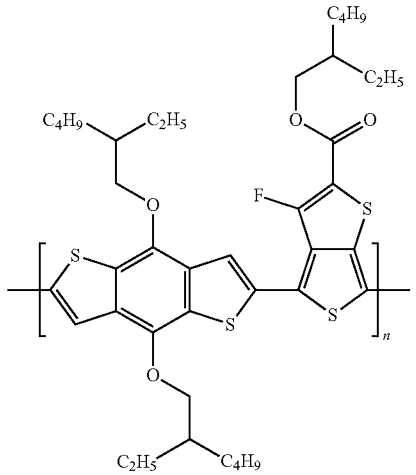
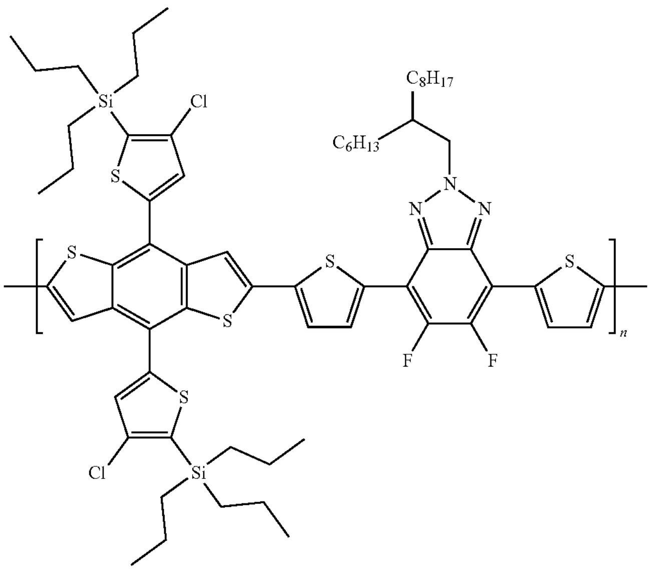

-continued
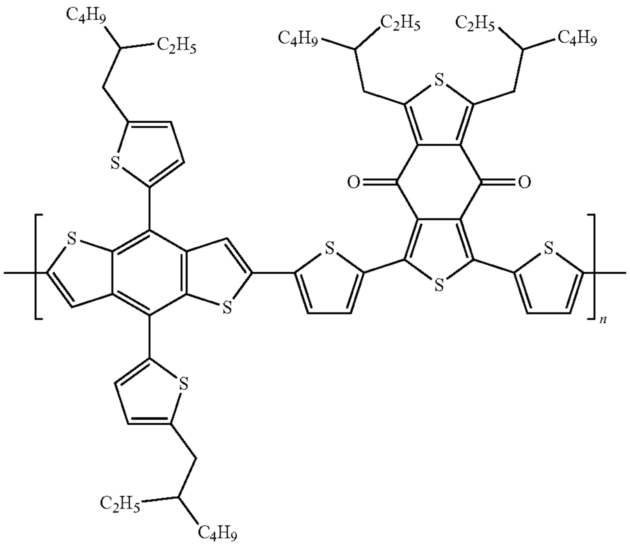
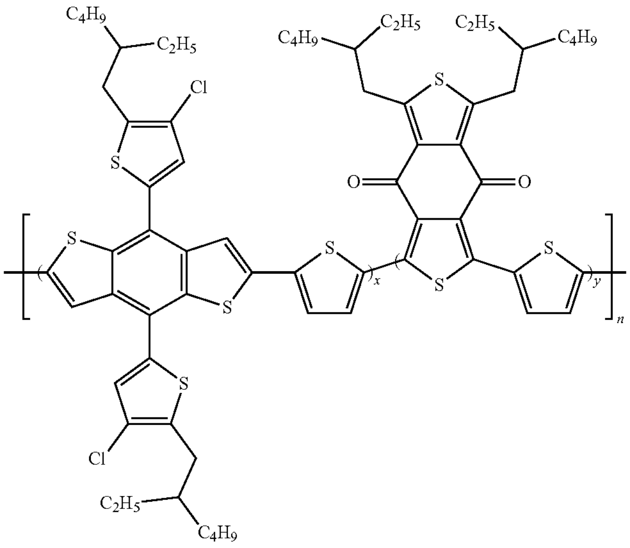
x = y = 0.5
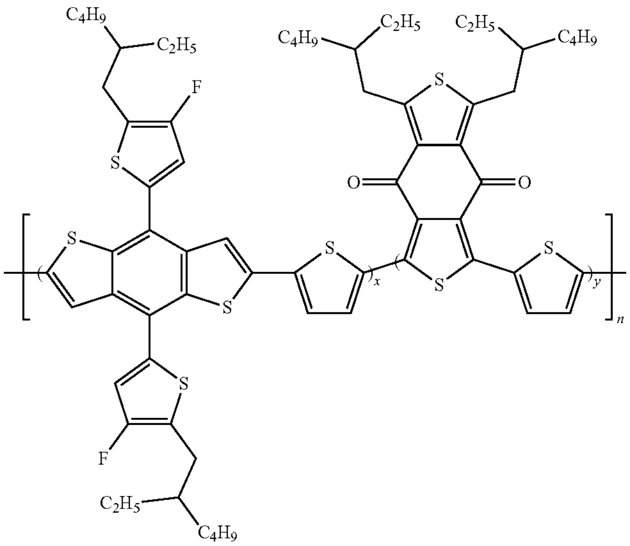
x = y = 0.5

-continued

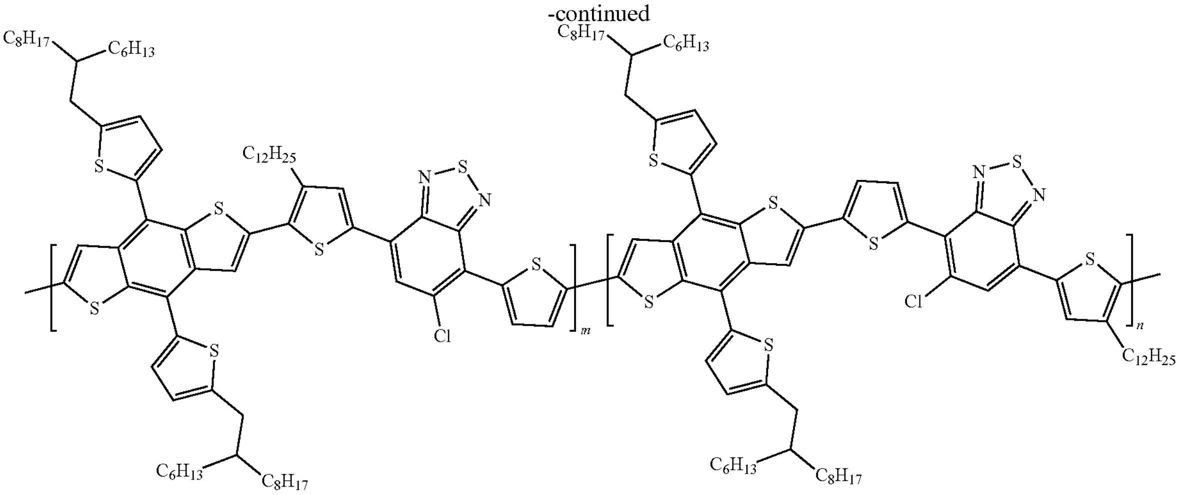

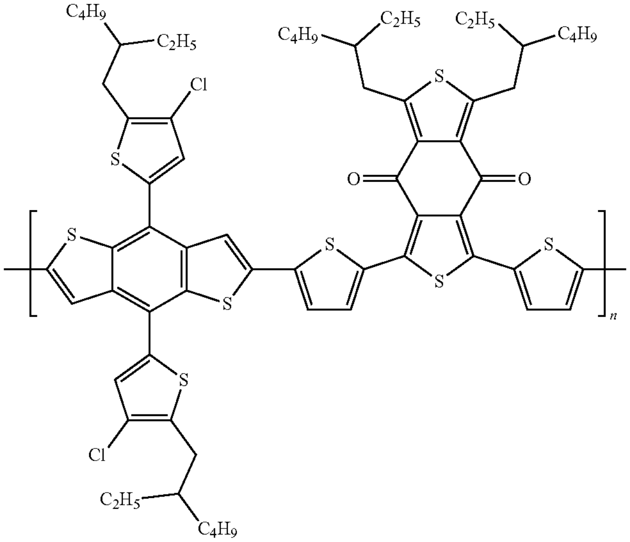

Wherein, m and n are positive integers.

The third category of the present invention is to provide an organic optoelectronic device which comprises a first electrode, an active layer and a second electrode. The active layer comprises at least one of a near-infrared organic small molecule with vinyl groups aforementioned. Wherein, the active layer is disposed between the first electrode and the second electrode, and at least one of the first electrode and the second electrode is a transparent or semi-transparent electrode.

Wherein, the organic optoelectronic device further comprises a first carrier transporting layer and a second carrier transporting layer. The first carrier transporting layer is disposed between the first electrode and the active layer. The active layer is disposed between the first carrier transporting layer and the second carrier transporting layer, and the second carrier transporting layer is disposed between the active layer and the second electrode.

Wherein, the active layer material further comprises at least one of the following structures:

(formula II)

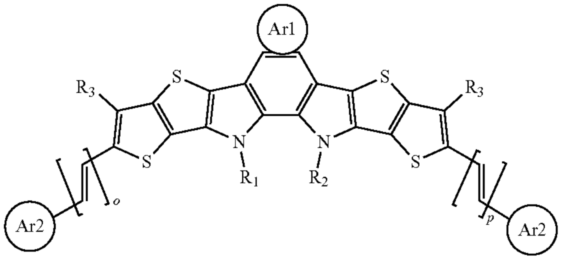

(formula III)

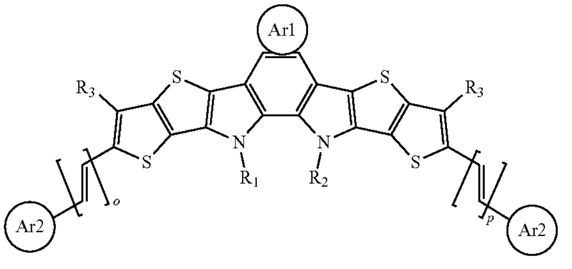

Wherein, o and p are independently selected from any integer from 0 to 2, and o+p>0. Ar1 is an electron-withdrawing group with a unilateral fused ring structure. Ar2 is a monocyclic or polycyclic structure containing ketone and an electron-withdrawing group, and has a double bond to bond other groups. $R_1$ is different from $R_2$; $R_1$, $R_2$ and $R_3$ respectively are one of the following groups: C1~C30 alkyl, C1~C30 silyl, C1~C30 alkoxy, C1~C30 alkylthio, C1~C30 haloalkyl, C2~C30 ester, C1~C30 alkylaryl, C1~C30 alkylheteroaryl, C1~C30 silylaryl, C1~C30 silylheteroaryl, C1~C30 alkoxyaryl, C1~C30 alkoxyhetero aryl, C1~C30 alkylthioaryl, C1~C30 alkylthioheteroaryl, C1~C30 haloalkylaryl, C1~C30 haloalkylheteroaryl, C2~C30 ester aryl and C2~C30 ester heteroaryl.

Compared with the prior art, the near-infrared organic small molecule with vinyl groups of the present invention is a non-fullerene acceptor material with a light absorption range of 900~1000 nm. In terms of material design, the present invention adds a vinyl structure to the non-fullerene acceptor, which can effectively expand the wavelength range of light absorption to 900~1000 nm. In addition, non-halogen solvents are used in the device manufacturing process to improve environmental friendliness, and still maintain good organic photodetector device performance and device stability performance.

BRIEF DESCRIPTION OF THE APPENDED DRAWINGS

Some of the embodiments will be described in detail, with reference to the following figures, wherein like designations denote like members, wherein.

Figure 12:
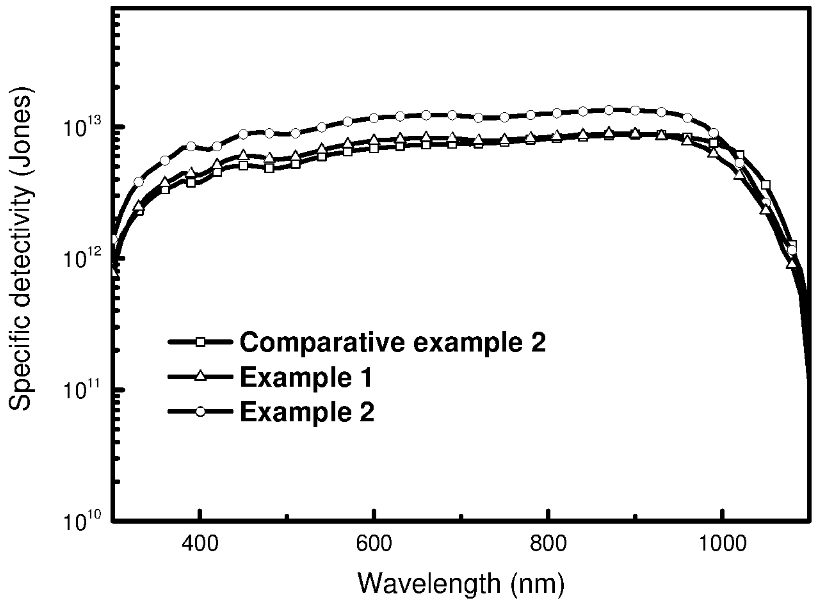

FIG. 12 shows the test results of dark current and detectivity of comparative example 2, example 1 and example 2 of the active layer material of the present invention.

DETAILED DESCRIPTION OF THE INVENTION

In order to make the advantages, spirit and features of the present invention easier and clearer, it will be detailed and discussed in the following with reference to the embodiments and the accompanying drawings. It is worth noting that the specific embodiments are merely representatives of the embodiments of the present invention, but it can be implemented in many different forms and is not limited to the embodiments described in this specification. Rather, these embodiments are provided so that this disclosure will be thorough and complete.

The terminology used in the various embodiments disclosed in the present invention is only for the purpose of describing specific embodiments, and is not intended to limit the various embodiments disclosed in the present invention. As used herein, singular forms also include plural forms unless the context clearly indicates otherwise. Unless otherwise defined, all terms (including technical and scientific terms) used in this specification have the same meanings as commonly understood by one of ordinary skill in the art to which the various embodiments disclosed herein belong. The above terms (such as those defined in commonly used dictionaries) will be interpreted as having the same meaning as the contextual meaning in the same technical field, and will not be interpreted as having an idealized or overly formal meaning, unless explicitly defined in the various embodiments disclosed herein.

In the description of this specification, the description of the reference terms "an embodiment", "a specific embodiment" and the like means that specific features, structures, materials, or characteristics described in connection with the embodiment are included in at least one embodiment of the present invention. In this specification, the schematic expressions of the above terms do not necessarily refer to the same embodiment. Furthermore, the particular features, structures, materials, or characteristics described may be combined in any suitable manner in any one or more embodiments.

DEFINITION

As used herein, "donor" material refers to a semiconductor material, such as an organic semiconductor material, having holes as a primary current or charge carrier. In some embodiments, when a P-type semiconductor material is deposited on a substrate, it can provide the hole mobility greater than about $10^{-5}$ $cm^2/Vs$. In the case of field effect devices, current on/off ratio of the P-type semiconductor material exhibits more than about 10.

As used herein, "acceptor" material refers to the semiconductor material, such as the organic semiconductor material, having electrons as the primary current or the charge carrier. In some embodiments, when a N-type semiconductor material is deposited on a substrate, it can provide the electron mobility greater than about $10^{-5}$ $cm^2/Vs$. In the case of field effect devices, current on/off ratio of the N-type semiconductor material exhibits more than about 10.

The "electron-withdrawing group" refers to a group or an atom with a stronger electron-withdrawing ability than that of hydrogen, that is, it has an electron-withdrawing inductive effect. The "electron-donating group" refers to a group or an atom whose electron-donating ability is stronger than that of hydrogen, that is, it has an electron-donating induction effect. The inductive effect is the effect that the bonding electron cloud moves in a certain direction on the atomic bond due to the difference in polarity (electronegativity) of atoms or groups in the molecule. The electron cloud tends to move towards the more electronegative groups or atoms.

"⁎" or "*" in the structures listed herein represents the available bonding positions of this structure, but not limited thereto.

As used herein, "component" (such as a thin film layer) may be considered "photoactive" if it contains one or more compounds that absorb photons to generate excitons for generating photocurrent.

As used herein, "solution proceeding" refers to a process in which a compound (e.g., a polymer), material, or composition can be used in a solution state, such as spin coating, printing (e.g., inkjet printing, gravure printing, and lithography printing), spray coating, slit coating, drop casting, dip coating, and blade coating.

As used herein, "annealing" refers to a post-deposition thermal treatment to a semi-crystalline polymer film for certain duration in the environment or under decompressed or pressurized environment. "Annealing temperature" refers to the temperature at which the polymer film or the mixed film of the polymer and other molecules can perform small-scale molecular movement and rearrangement during the annealing process. Without limitation by any particular theory, it is believed that annealing can lead to an increase in crystallinity in the polymer film and enhance the carrier mobility of the polymer film or a mixed film formed by the polymer and other molecules, and the molecules are arranged alternately to achieve the effect of independent transporting paths of effective electrons and holes.

Dark current ($J_d$) as used herein also known as no-illumination current, refers to the current flows in an opto-electronic device in the absence of light irradiation.

The responsibility (R) and the detectivity (D) as used herein are based on measuring the dark current and external quantum efficiency (EQE) of the organic photodetector, and are calculated by the following formula:

$$R(\lambda) = EQE\frac{\lambda q}{hc},$$

$$D = \frac{R}{\sqrt{2qJ_d}}$$

Wherein, λ is the wavelength, q is the elementary charge ($1.602\times10^{-19}$ Coulombs), h is Planck's constant ($6.626\times10^{-34}$ $m^2$ kg/s), c is the speed of light ($3\times10^8$ m/sec), and $J_d$ is the dark current.

In an embodiment, a near-infrared organic small molecule with vinyl group of the present invention is a seven-membered fused ring compound bridged by vinyl groups. In detail, it comprises a structure of formula 1:

(formula I)

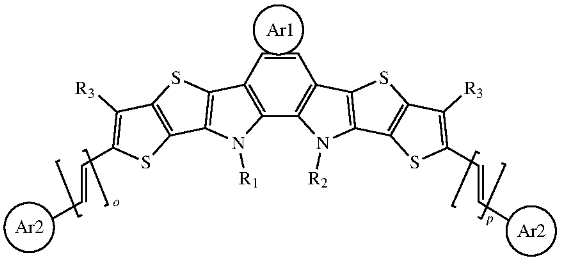

Wherein, o and p are independently selected from any integer from 0 to 2, and o+p>0. Ar1 is an electron-withdrawing group with a unilateral fused ring structure. Specifically, the unilateral fused ring structure means that one side is bonded to other structures in the form of a fused ring. Ar2 is a monocyclic or polycyclic structure containing ketone and an electron-withdrawing group, and has a double bond to bond other groups. $R_1$ is different from $R_2$, and $R_1$, $R_2$ and $R_3$ respectively are one of the following groups: C1~C30 alkyl, C1~C30 silyl, C1~C30 alkoxy, C1~C30 alkylthio, C1~C30 haloalkyl, C2~C30 ester, C1~C30 alkylaryl, C1~C30 alkylheteroaryl, C1~C30 silylaryl, C1~C30 silylheteroaryl, C1~C30 alkoxyaryl, C1~C30 alkoxyheteroaryl, C1~C30 alkylthio aryl, C1~C30 alkylthiohetero aryl, C1~C30 haloalkylaryl, C1~C30 haloalkylheteroaryl, C2~C30 ester aryl and C2~C30 ester heteroaryl.

In this embodiment, Ar1 further comprises a five-membered heterocyclic or a six-membered heterocyclic structure having at least one heteroatom, and the heteroatom is independently selected from at least one of S, N, O and Se.

In practice, Ar1 is one of the following structures:

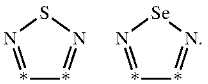

In this embodiment, Ar2 is a monocyclic or polycyclic derivative containing ketone and an electron-withdrawing group. In a preferred embodiment, Ar2 further comprises a fused ring structure of at least one of a five-membered ring and a six-membered ring, and the fused ring structure comprises at least one of C═O and cyano.

In practice, Ar2 is one of the following structures:

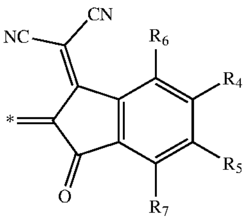

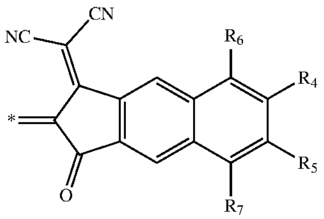

-continued

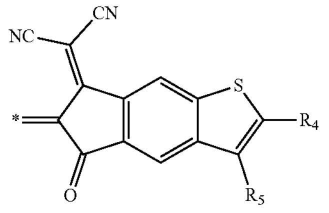

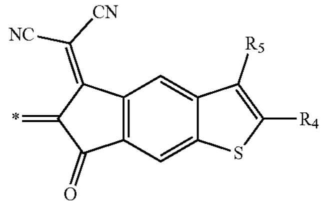

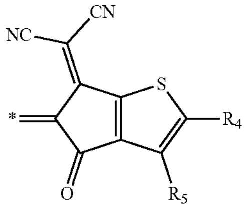

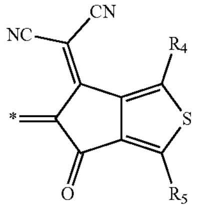

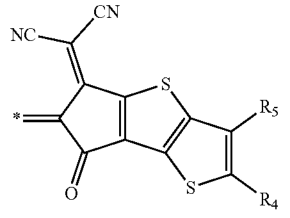

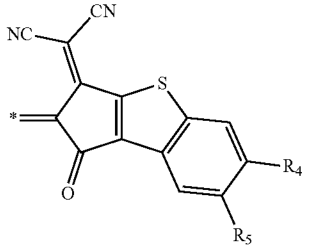

-continued

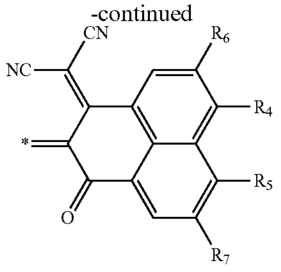

Wherein, $R_4$, $R_5$, $R_6$ and $R_7$ respectively are one of the following groups: C1~C30 alkyl, C1~C30 silyl, C1~C30 alkoxy, C1~C30 haloalkyl, halogen, cyano and hydrogen.

Regarding $R_1$ and $R_2$, in practical applications, organic optoelectronic devices manufactured by wet process usually introduce long carbon chains into organic small molecules, so that organic small molecules can be dissolved in organic solvents. Since different carbon chains usually have different characteristics, the choice of carbon chains for $R_1$ and $R_2$ is very important. Short carbon chains with fewer carbon numbers usually make the material highly crystalline and have good arrangement and electrical conductivity. However, the disadvantage of the short carbon chains is that it sacrifices the solubility of organic small molecules, and the device manufacturing process is usually limited to halogen-containing solvent processes or thermal processes. Long carbon chains with more carbon numbers can make organic small molecules have good solubility, and increase the feasibility of the process, allowing the device process to use non-halogen solvents and room temperature processes. However, the disadvantage of the long carbon chains is that the arrangement and conductivity of organic small molecules will be sacrificed.

In addition to the carbon chain selection of organic small molecules, the selection of organic solvents is also very important. Halogen-containing solvents (such as chloroform, chlorobenzene, and o-dichlorobenzene) have high polarity, can effectively dissolve materials, and promote molecular alignment during film formation. However, the halogen-containing solvents are not friendly to the environment and cause great harm to the human body, so they are a major concern in terms of commercialization. In order to use non-halogen solvents (such as toluene, o-xylene, mesitylene, tetrahydrofuran and 2-methyltetrahydrofuran) as the device manufacturing process, the structural design of organic small molecules usually requires the introduction of long carbon chains with more carbon numbers, so that the materials have good solubility and film-forming properties in non-halogen solvents.

In order to solve the above problems, the present invention designs an organic small molecule with asymmetric carbon chains, which provides a new choice in the balance of solubility, arrangement and conductivity. In addition, in terms of material design in the present invention, we add vinyl structures to non-fullerene acceptors, which can effectively expand the light absorption range to a wavelength of 900~1000 nm. The manufacturing process of the organic optoelectronic device of the present invention uses non-halogen solvents to improve environmental friendliness, and still allows the organic optoelectronic device to maintain good organic photodetector device performance and device stability performance.

The near-infrared organic small molecule with vinyl groups of the present invention may comprise the following examples A1~A14:

A1
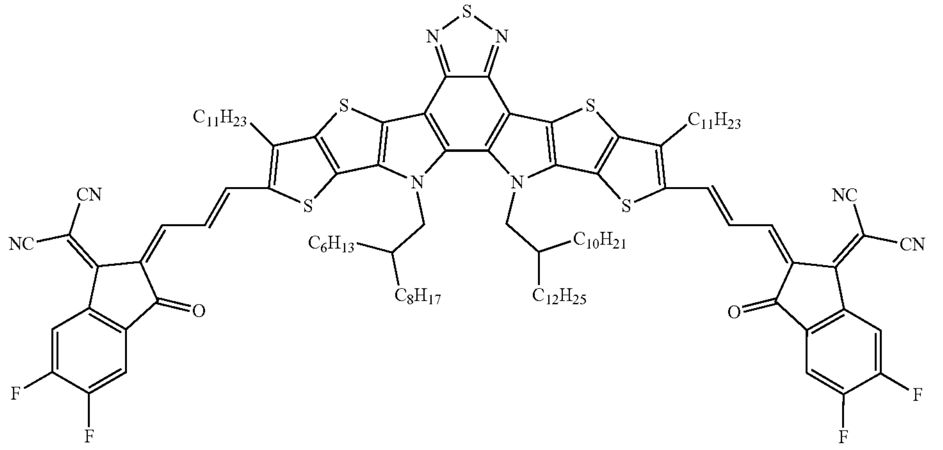
A2
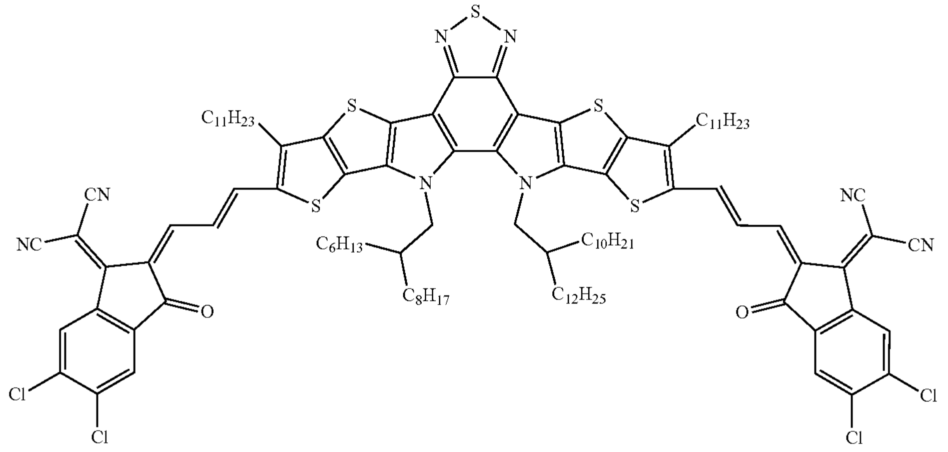
A3
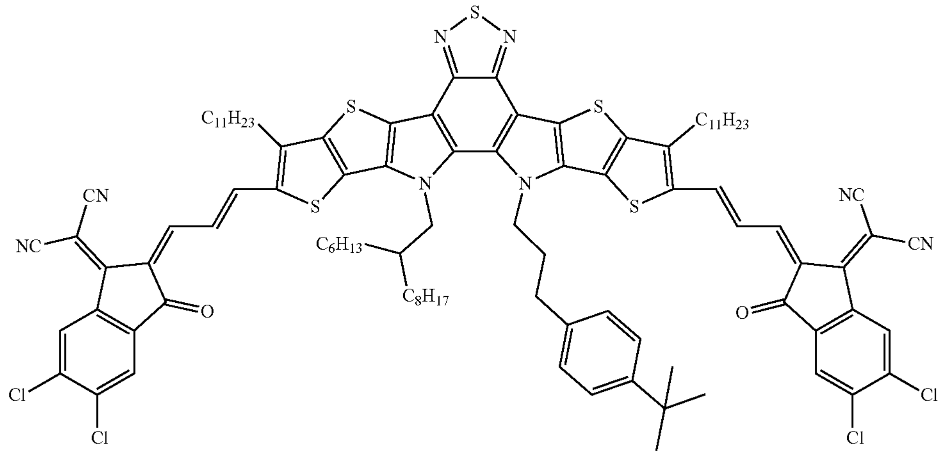

-continued
A4
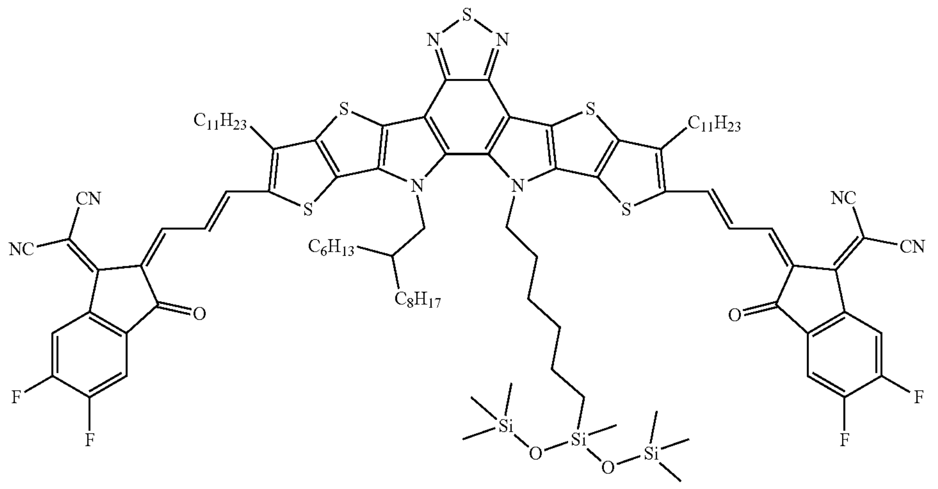
A5
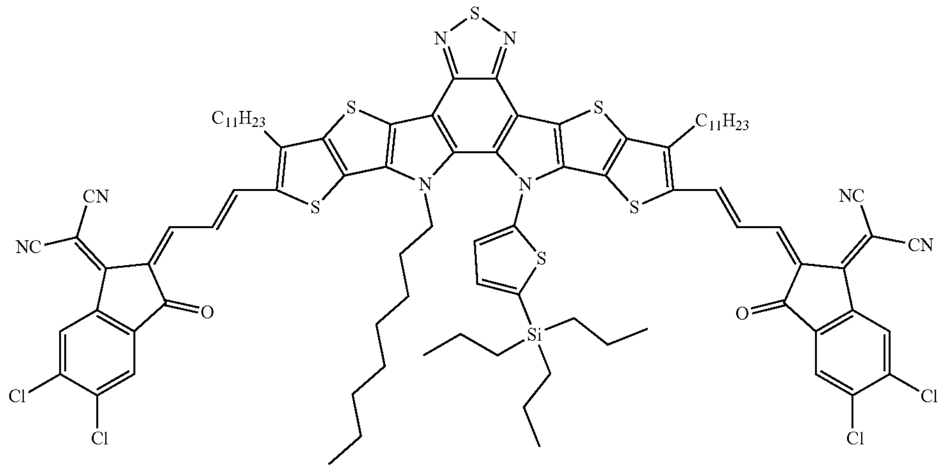
A6
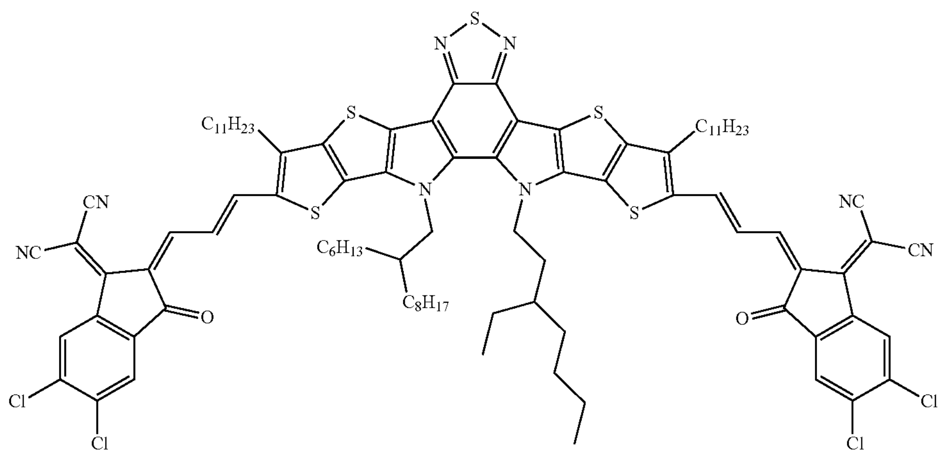

-continued
A7
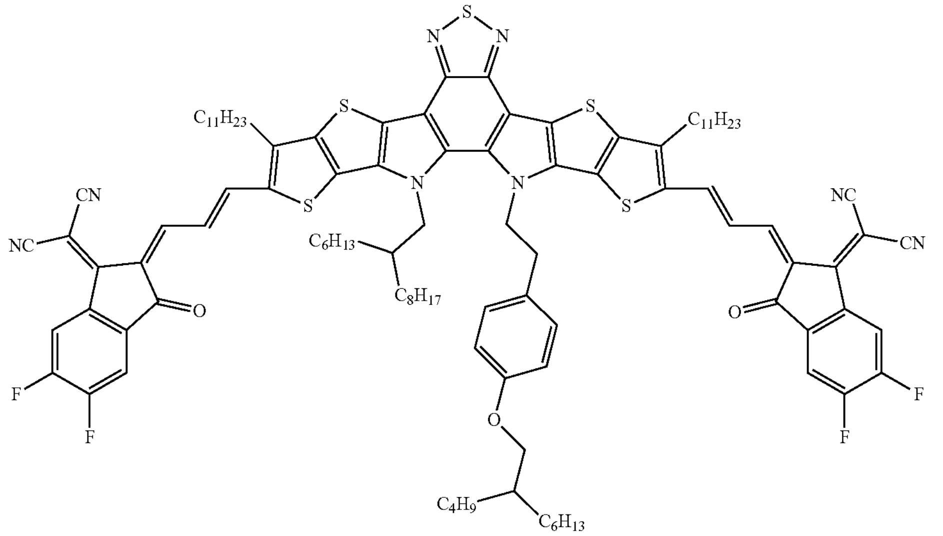
A8
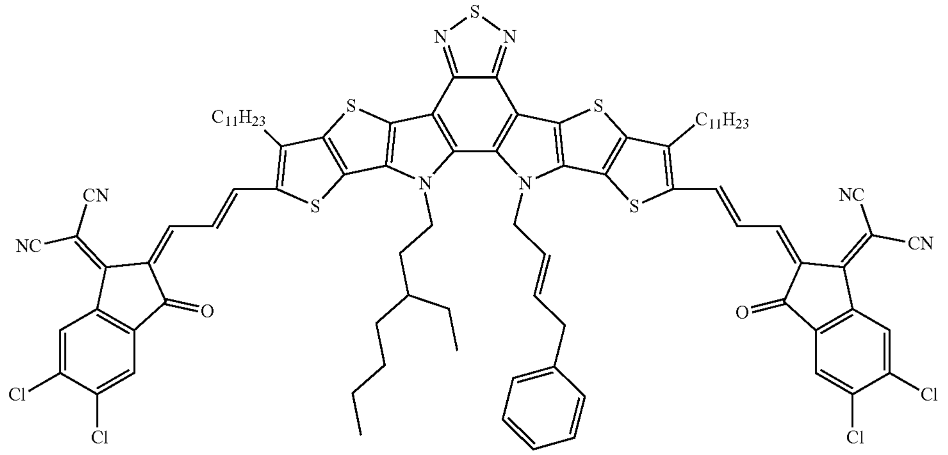
A9
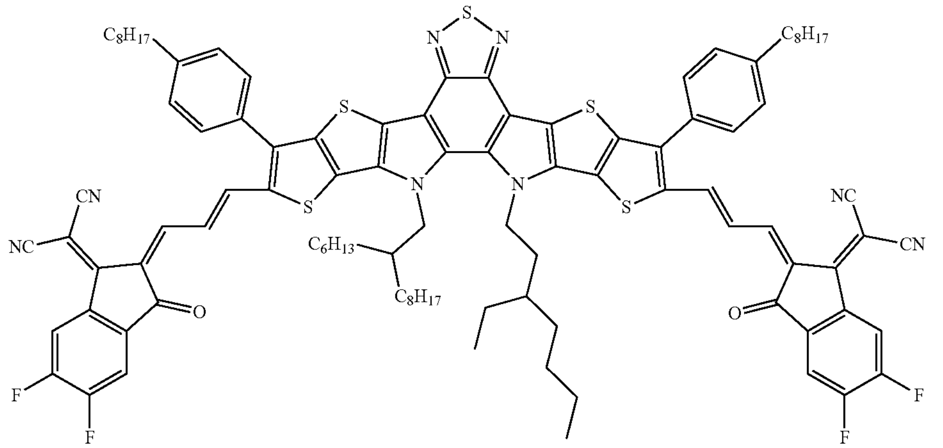

-continued
A10
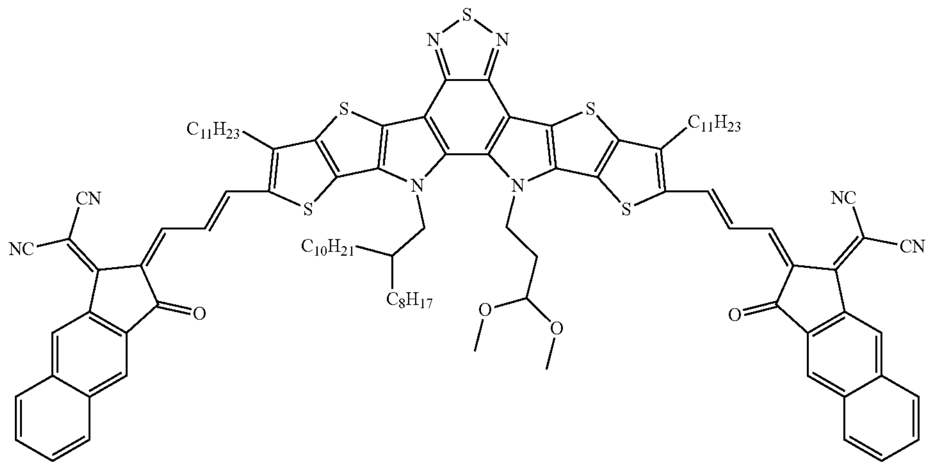
A11
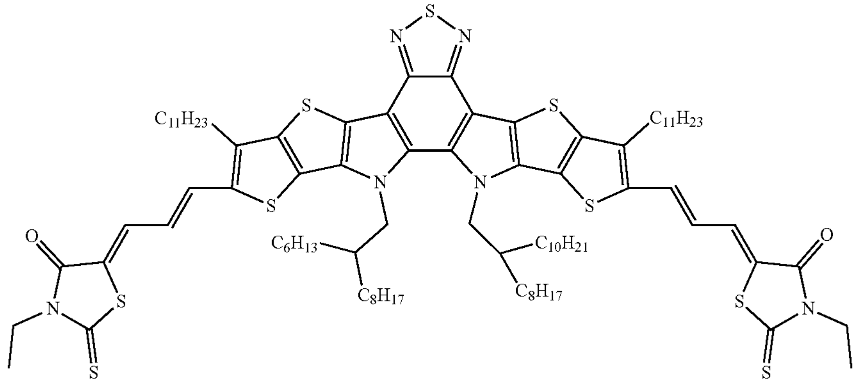
A12
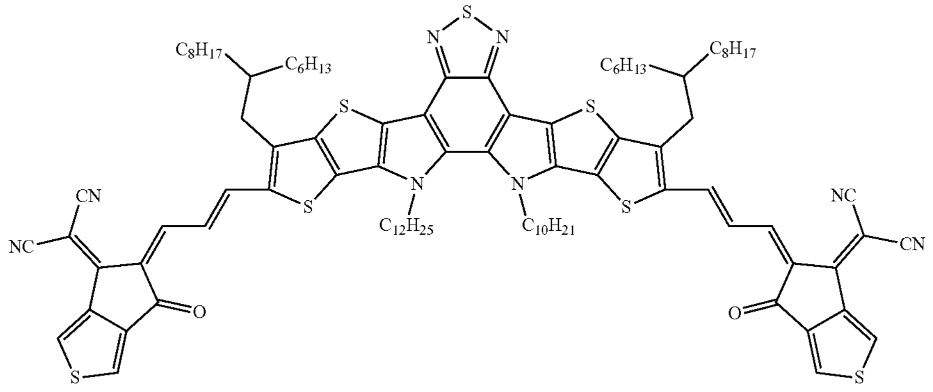

-continued

A13

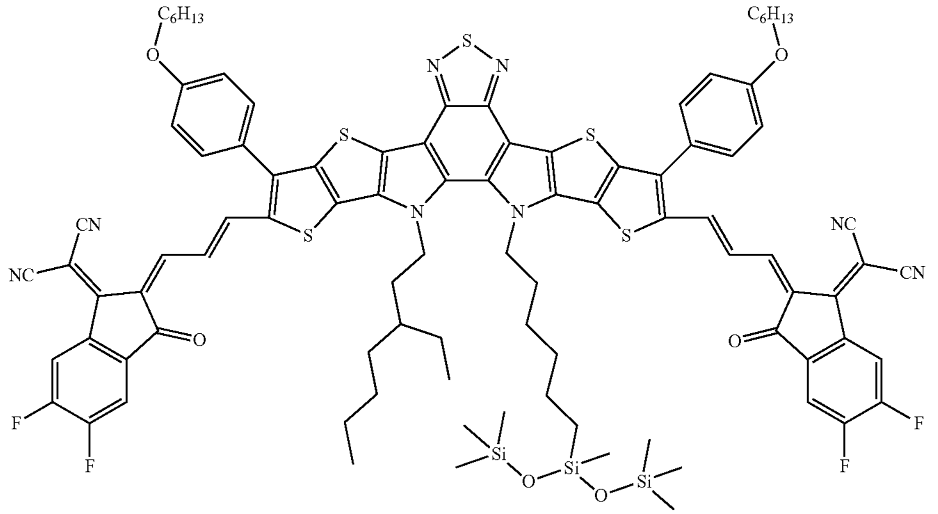

A14

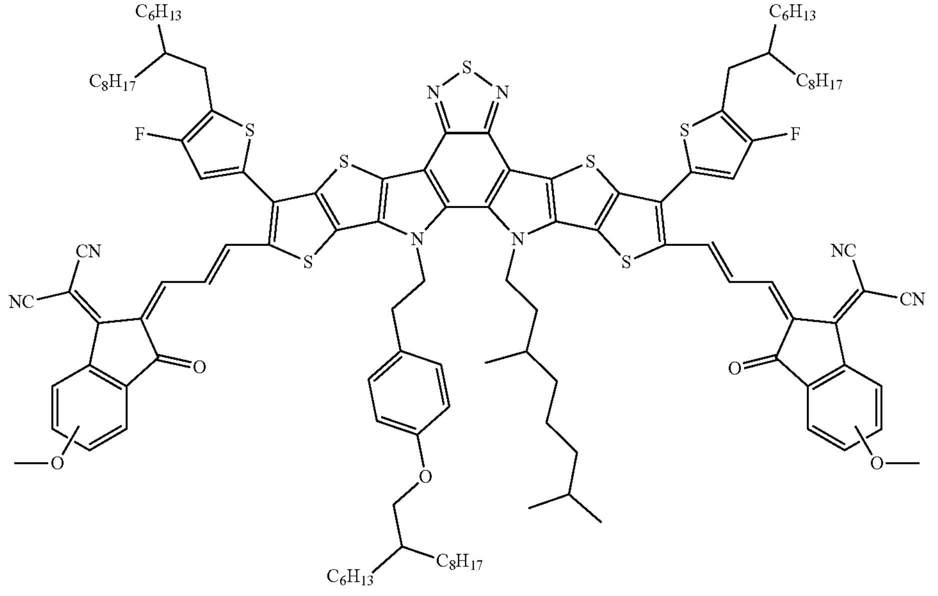

It should be understood that the above-listed embodiments are only intended to allow the person skilled in the art to understand the structure and composition of the present invention more clearly, and are not limited thereto.

However, since the synthetic pathway of an asymmetric organic small molecule needs to introduce different carbon chains into the structure in two stages, this will greatly reduce the yield. Therefore, the present invention also designs a synthetic route to obtain a formula combination containing an asymmetric organic small molecule and a symmetrical organic small molecule, trying to find the formulation with the best efficiency. In this synthetic route, two carbon chains are simultaneously introduced into the structure in the same step (this part will be presented in the following synthetic steps). Therefore, the synthesized mixture contains not only the aforementioned asymmetric organic small molecule, but also two symmetrical organic small molecules with different carbon chains. Next, the above-mentioned asymmetric near-infrared organic small molecule with vinyl groups and mixtures containing asymmetric and symmetrical near-infrared organic small molecules with vinyl groups are used as the active layer material respectively to confirm the efficiency of the two made into organic optoelectronic devices.

In view of this, an embodiment of the present invention provides an active layer material, which comprises an acceptor material and a donor material. The acceptor material comprises the near-infrared organic small molecule with vinyl groups comprising the structure of the formula I. The donor material contains at least one organic conjugated polymer. In detail, the acceptor material of this embodiment only comprises the asymmetric near-infrared organic small molecule with vinyl groups. It should be noted that, although the acceptor material and the donor material are described in singular here, plural cases are also included.

Further, another embodiment of the present invention provides an active layer material, which also comprises acceptor material and donor material. Different from the former, this embodiment comprises asymmetric and symmetrical near-infrared organic small molecules with vinyl groups. Therefore, the near-infrared organic small molecule with vinyl groups of the acceptor material in this embodiment not only comprises the structure of formula 1, but also comprises at least one of the following structures:

(formula II)

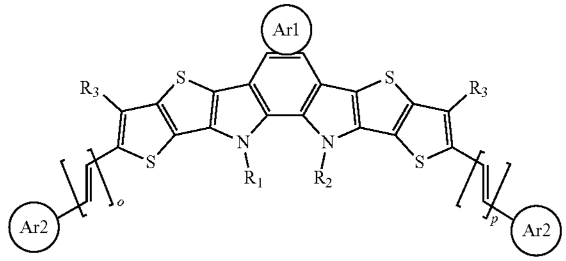

(formula III)

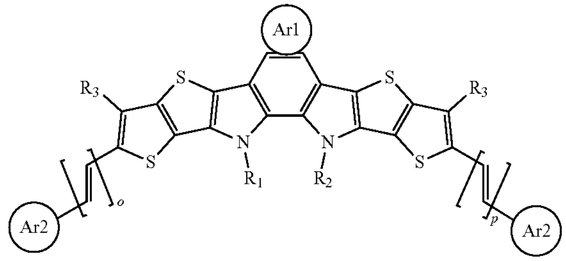

Wherein, o and p are independently selected from any integer from 0 to 2, and o+p>0. Arl is an electron-withdrawing group with a unilateral fused ring structure. Ar2 is a monocyclic or polycyclic structure containing ketone and an electron-withdrawing group, and has a double bond to bond other groups. $R_1$ is different from $R_2$, and $R_1$, $R_2$ and $R_3$ respectively are one of the following groups: C1~C30 alkyl, C1~C30 silyl, C1~C30 alkoxy, C1~C30 alkylthio, C1~C30 haloalkyl, C2~C30 ester, C1~C30 alkylaryl, C1~C30 alkylhetero aryl, C1~C30 silylaryl, C1~C30 s ilylhetero aryl, C1~C30 alkoxyaryl, C1~C30 alkoxyheteroaryl, C1~C30 alkylthioaryl, C1~C30 alkylthioheteroaryl, C1~C30 haloalkylaryl, C1~C30 haloalkylheteroaryl, C2~C30 ester aryl and C2~C30 ester heteroaryl.

In practice, when the acceptor material comprises the structure of formula I, formula II and formula III at the same time, the molar ratios of the structure of formula I, formula II and formula III are a, b and c respectively, and $0<a\leq1$, $0<b\leq1$, $0<c\leq1$, and a+b+c=1. Due to the steric hindrance of the structure, the introduction of long carbon chains will be unfavorable for the synthesis of organic small molecules with long carbon chains. Therefore, under the effect of steric hindrance, when the carbon number of $R_2$ is greater than that of $R_1$, a>b>c; when the carbon number of $R_2$ is smaller than that of $R_1$, a>c>b. However, it should be noted that in addition to steric hindrance, factors including the selection of reactants and whether there are other functional groups on the carbon chain will affect the relationship between a, b and c.

In practice, the donor material of the present invention comprises at least one thiophene in its structure. Specifically, the donor material of the present invention is one of the following structures:

Polymer 1

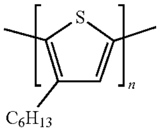

Polymer 2

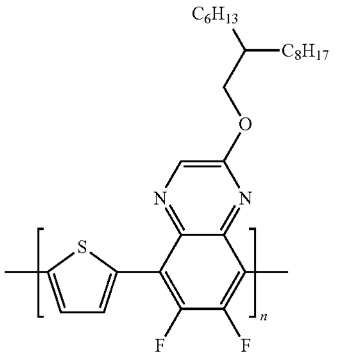

-continued
Polymer 3
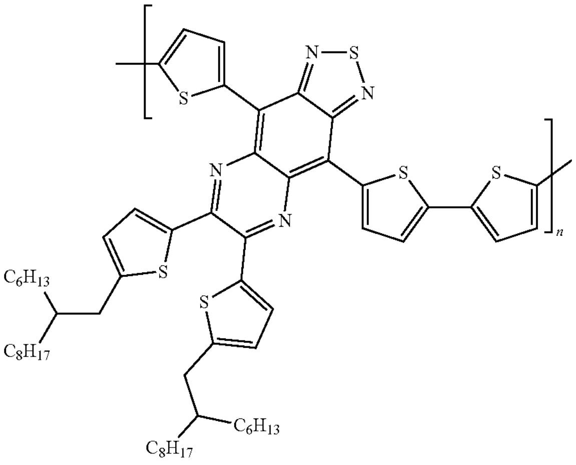
Polymer 4
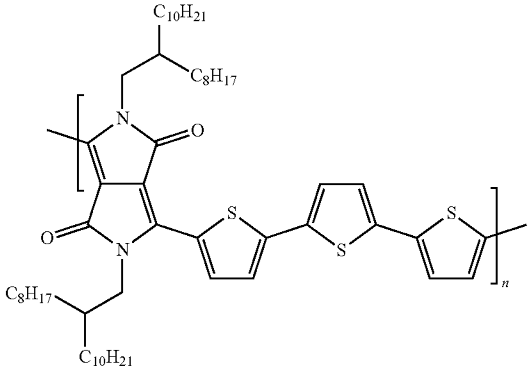
Polymer 5
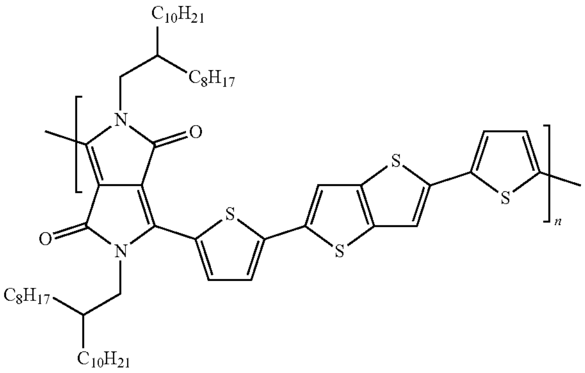
Polymer 6
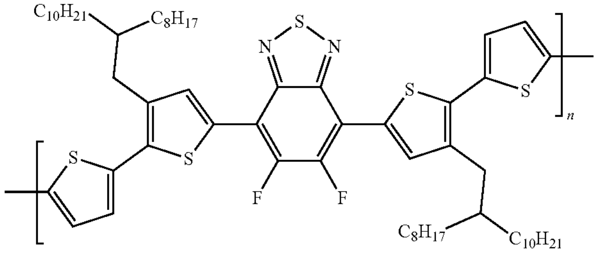
Polymer 7
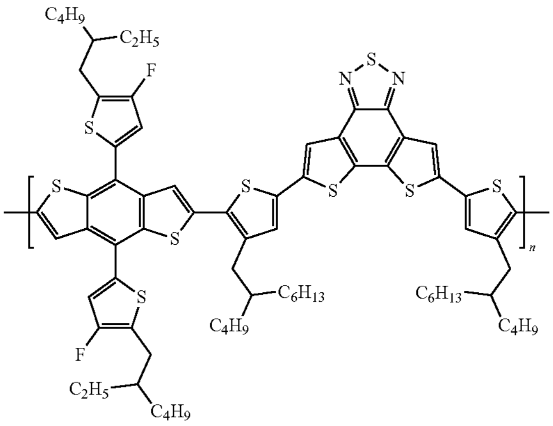
Polymer 8
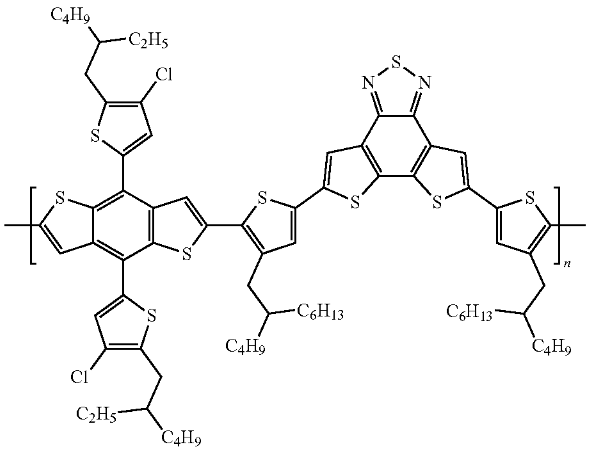

-continued
Polymer 9
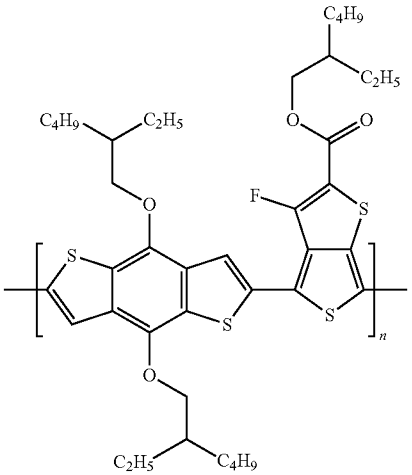
Polymer 10
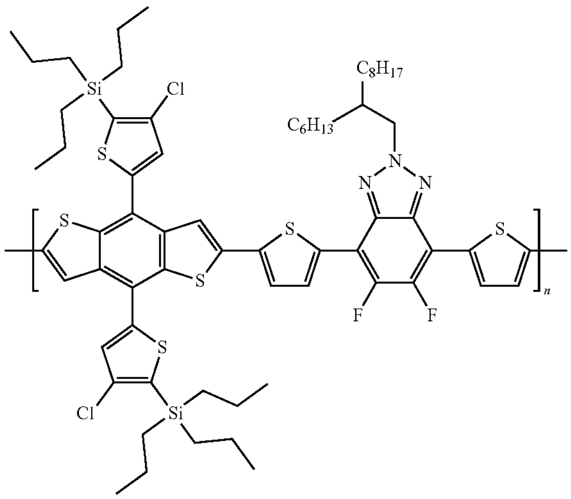
Polymer 11
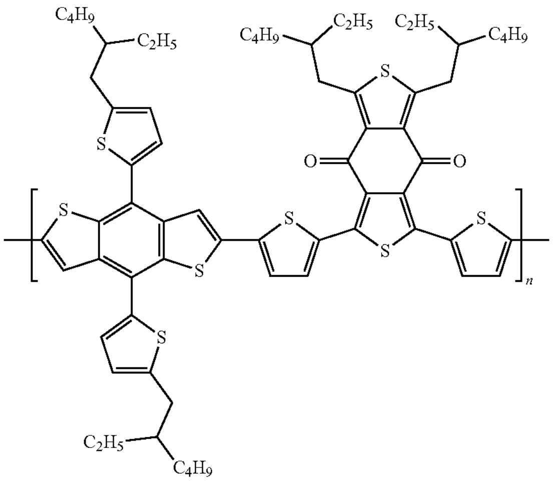
Polymer 12
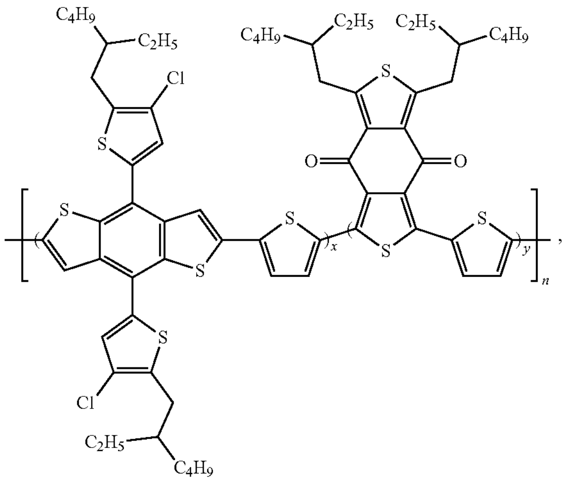
x = y = 0.5
Polymer 13
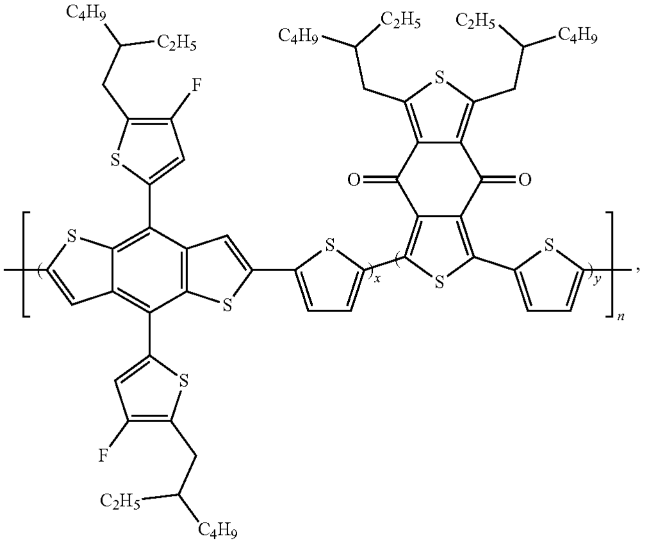
x = y = 0.5

-continued

Polymer 14

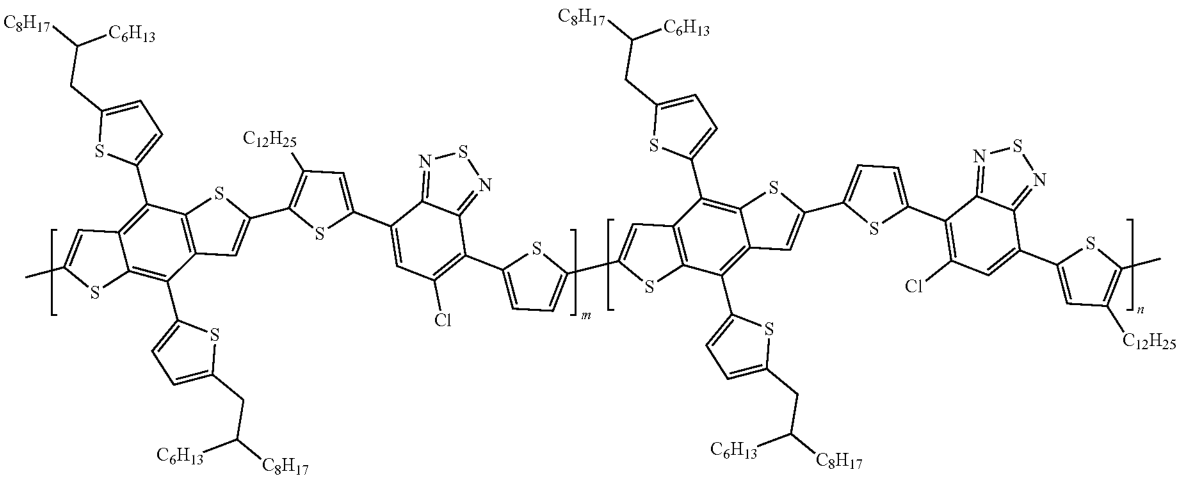

Polymer 15

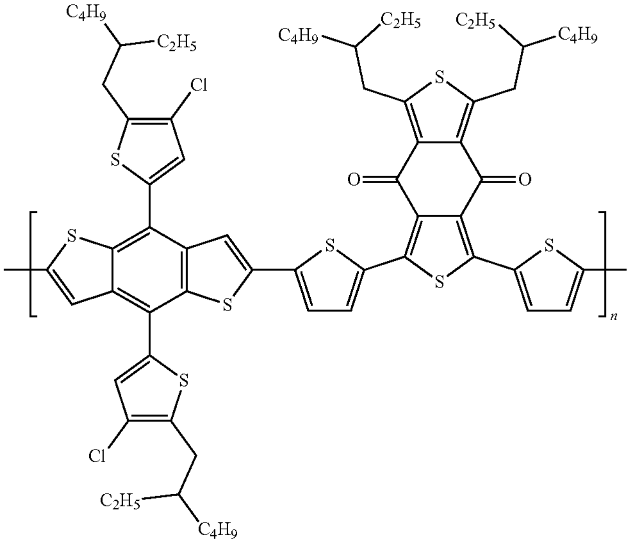

Wherein, since the above structures are polymers, m and n are the number of molecules and are positive integers.

Figure 1:
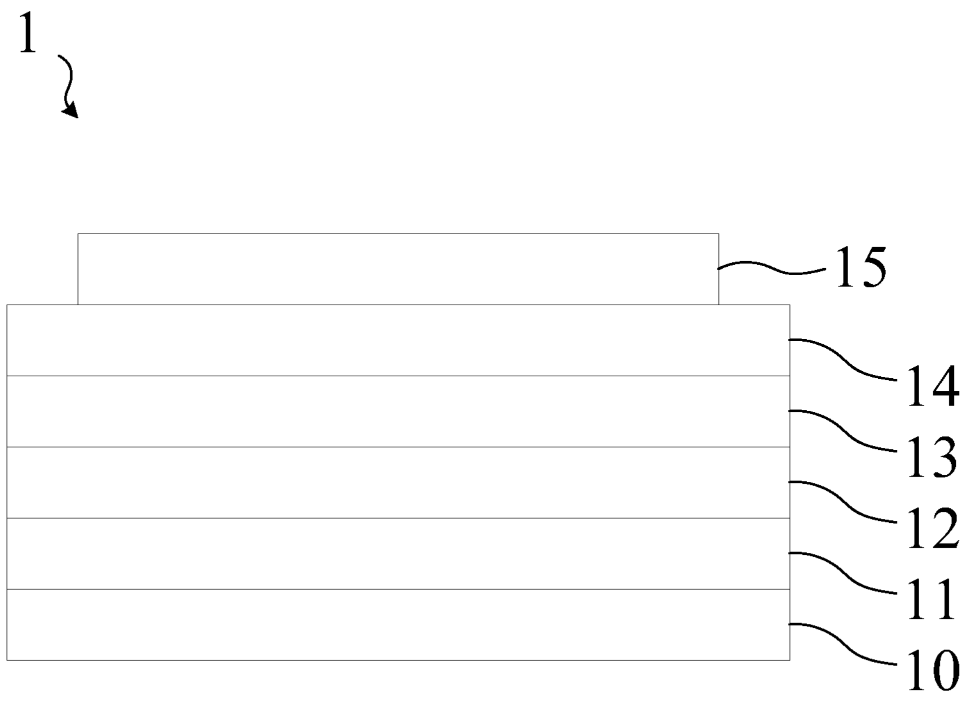
FIG. 1 shows a schematic structural diagram of one embodiment of an organic optoelectronic device of the present invention.

Please refer to FIG. 1. FIG. 1 shows a schematic structural diagram of one embodiment of an organic optoelectronic device of the present invention. As shown in FIG. 1, in an embodiment, the present invention further provides an organic optoelectronic device 1, which comprises a first electrode 11, a second electrode 15 and an active layer 13. The active layer 13 is disposed between the first electrode 11 and the second electrode 15. In one embodiment, the active layer 13 comprises the near-infrared organic small molecule with vinyl groups with formula I. In another embodiment, the active layer 13 further comprises the near-infrared organic small molecule with vinyl groups with formula II and formula III. The organic optoelectronic device 1 may have a stacked structure, which sequentially includes a substrate 10, the first electrode 11 (transparent or semi-transparent electrode), a first carrier transporting layer 12, the active layer 13, a second carrier transporting layer 14 and the second electrode 15. Wherein, the first carrier transporting layer is one of an electron transporting layer and a hole transporting layer, and the second carrier transporting layer is the other one. In detail, when the first carrier transporting layer is the electron transport layer, the second carrier transporting layer is the hole transport layer, which is an inverted stacked structure; when the first carrier transporting layer is the hole transporting layer, the second carrier transporting layer is an electron transporting layer, which is a conventional stacked structure. In practice, the organic optoelectronic device 1 may comprise an organic photovoltaic device, an organic photodetector device, or an organic light emitting diode.

In order to more clearly illustrate the near-infrared organic small molecule with vinyl groups of the present invention, the following description will be taken as an example of A2, and it will be further prepared as an active layer material and an organic optoelectronic device for material testing and device testing.

Preparation of acceptor materials A2, A2-1, A2-2 and mixture A2 of active layer materials:

An Acceptor Material A2 of an Active Layer Material Synthesized from M1:

Synthesis of M3:

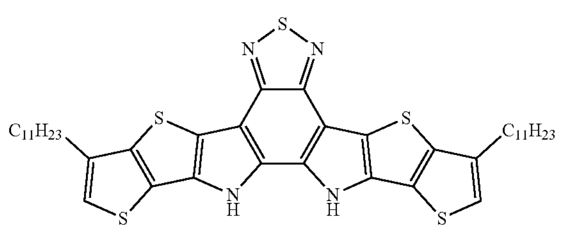

M1

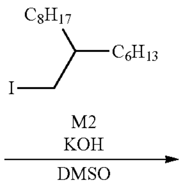

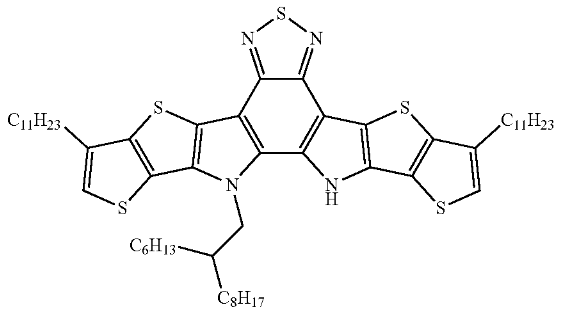

M3

M1 (1.0 g, 1.3 mmol), and potassium hydroxide (KOH, 0.2 g, 4.0 mmol) were placed into a 250 mL three-neck reaction flask. Dimethyl sulfoxide (DMSO, 30 mL) was added, and the reaction mixture was stirred at room temperature for 30 minutes, and then 1-iodo-2-hexyldodecane (0.9 g, 2.7 mmol) was added. The temperature was raised to 80 °C for 18 hours. The reaction was cooled to room temperature and extracted three times with ethyl acetate/water (EA/$H_2O$). The organic layer was collected and was dried with magnesium sulfate, and the solvent was removed. The crude product was purified by a silica gel column (eluent: heptane/dichloromethane=3/1) to obtain the product M3 as a red solid (0.7 g, yield 54%). $^1H$ NMR (500 MHz, $CDCl_3$): δ 8.71 (s, 1H), 6.96-6.95 (m, 2H), 4.33-4.32 (m, 2H), 2.79-2.74 (m, 4H), 2.10 (m, 1H), 1.86-1.80 (m, 4H), 1.49-1.15 (m, 56H), 0.90-0.78 (m, 12H).

Synthesis of M5:

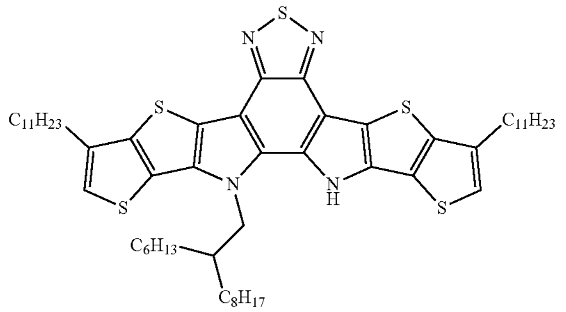

M3

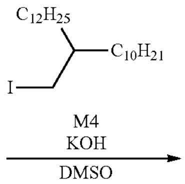

-continued

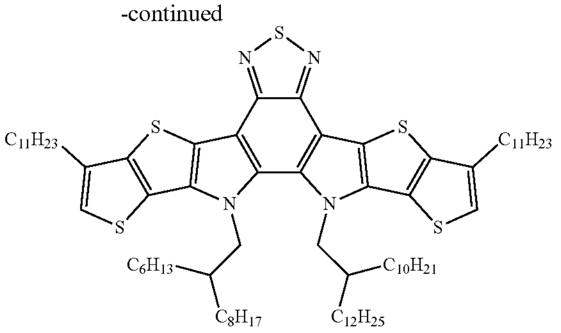

M5

M3 (0.7 g, 0.7 mmol), and potassium hydroxide (KOH, 0.1 g, 2.1 mmol) were placed into a 100 mL three-neck reaction flask. Dimethyl sulfoxide (DMSO, 21 mL) was added, and the reaction mixture was stirred at room temperature for 30 minutes. 1-iodo-2-decyltetradecane (0.7 g, 1.4 mmol) was added at room temperature. The temperature was raised to 80 °C for 18 hours. The reaction was cooled to room temperature and extracted three times with ethyl acetate/water (EA/$H_2O$). The organic layer was collected and was dried with magnesium sulfate, and the solvent was removed. The crude product was purified by a silica gel column (eluent: heptane/dichloromethane=3/1) to obtain the product M5 as a red solid (0.7 g, yield 74%). $^1$H NMR (500 MHz, $CDCl_3$): δ 7.01 (s, 2H), 4.59-4.57 (m, 4H), 2.83-2.80 (m, 4H), 2.06 (s, 2H), 1.85 (m, 4H), 1.43-1.03 (m, 96H), 0.89-0.82 (m, 18H).

Synthesis of M6:

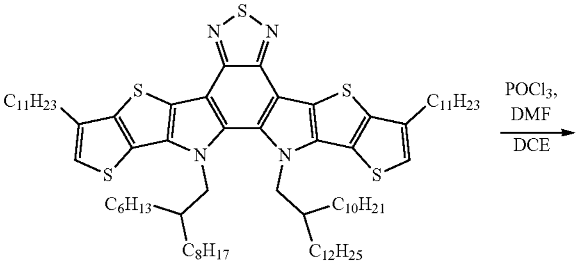

M5

-continued

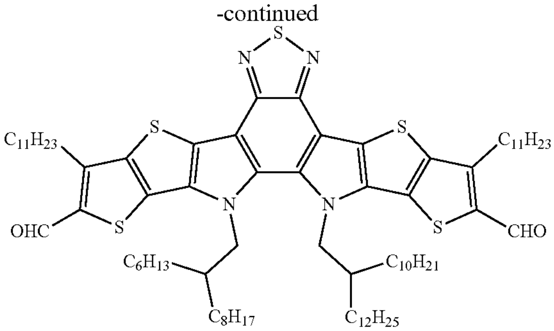

M6

In an ice bath, phosphorus oxychloride ($POCl_3$, 0.5 g, 3.2 mmol) and dimethylformamide (DMF, 2.0 g, 26.8 mmol) were mixed in a 100 mL three-necked reaction flask and stirred for 30 minutes to form a Vilsmeier reagent. M5 (0.7 g, 0.5 mmol) was placed into another 100 mL three-necked reaction flask. Dichloroethane (DCE, 35 mL) was added and stirred, then the Vilsmeier reagent was added. The reaction was heated to 60 °C for 18 hours. The reaction was cooled to room temperature and extracted three times with dichloromethane/water. The organic layer was collected and was dried with magnesium sulfate, and the solvent was removed. The crude product was purified by a silica gel column (eluent: heptane/dichloromethane=1/1) to obtain the product M6 as a red solid (0.6 g, yield 88%). $^1$H NMR (500 MHz, $CDCl_3$): δ 10.14 (s, 2H), 4.62 (d, J=8.4 Hz, 4H), 3.20-3.18 (m, 4H), 2.06 (s, 2H), 1.90 (m, 4H), 1.48-1.13 (m, 96H), 0.89-0.67 (m, 18H).

Synthesis of M8:

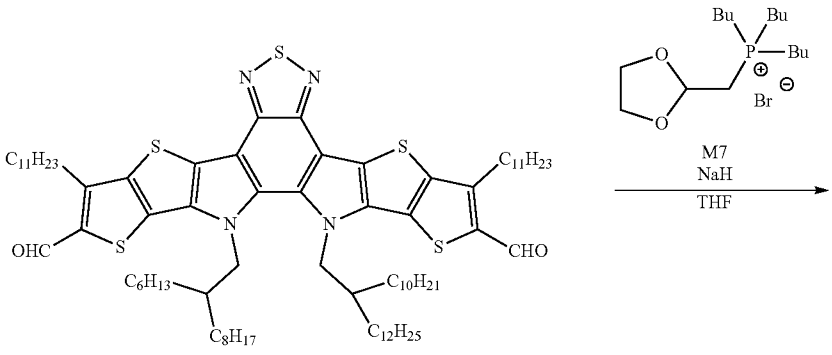

M6

-continued

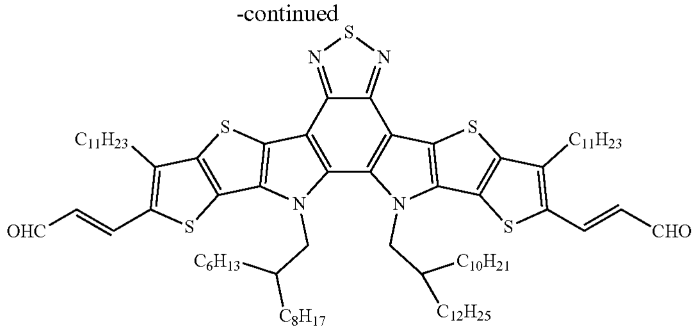

M8

M6 (0.6 g, 0.4 mmol), M7 (0.6 g, 1.8 mmol), and sodium hydride (NaH, 0.06 g, 2.6 mmol) were mixed in a 100 mL three-necked reaction flask. Anhydrous tetrahydrofuran (THF, 30 mL) was added and the reaction was stirred for 18 hours. In an ice bath, dilute hydrochloric acid (10%, 3 mL) was added and reacted for 30 minutes. The reaction was extracted three times with ethyl acetate/water. The organic layer was collected and was dried with magnesium sulfate, and the solvent was removed. The crude product was purified by a silica gel column (eluent: heptane/dichloromethane=1/1) to obtain the product M8 as a red solid (0.6 g, yield 96%). $^1$H NMR (500 MHz, CDCl$^3$): δ 9.70 (d, J=7.5 Hz, 2H), 7.78 (d, J=15.5 Hz, 2H), 6.55-6.51 (m, 2H), 4.60-4.57 (m, 4H), 3.00-2.97 (m, 4H), 2.01 (s, 2H), 1.86 (m, 4H), 1.48-1.22 (m, 96H), 1.03-0.68 (m, 18H).

Synthesis of A2:

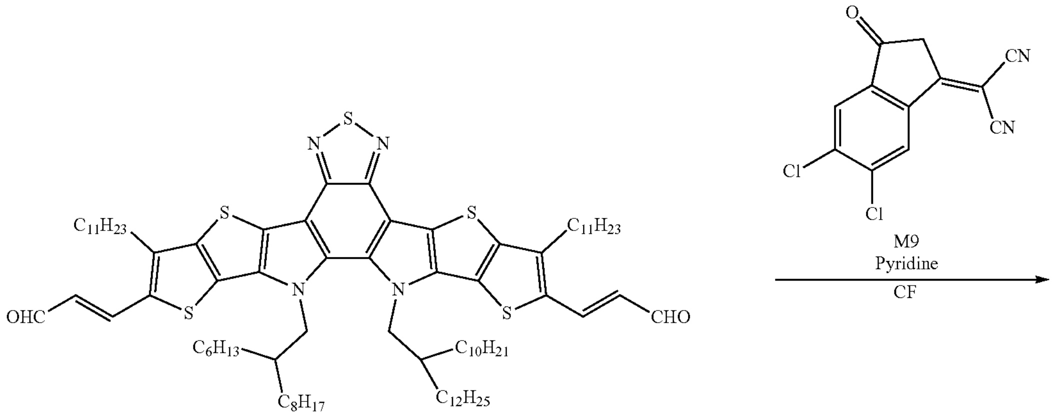

M8

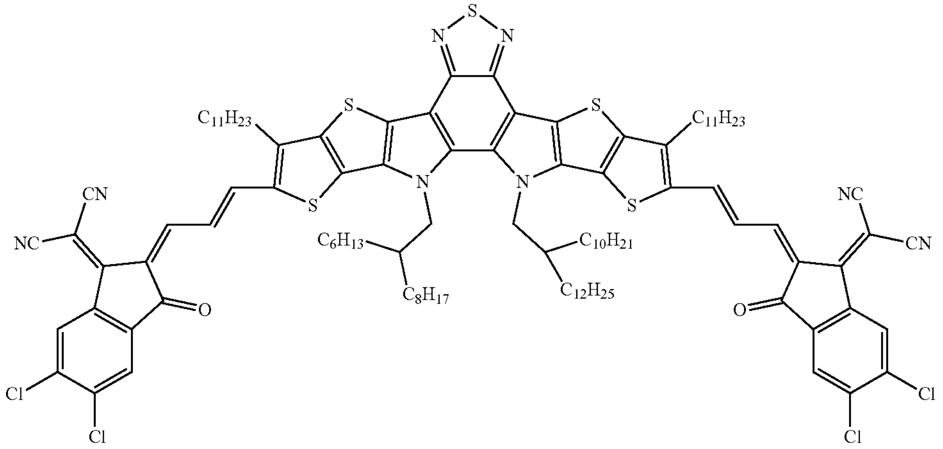

A2

M8 (0.3 g, 0.21 mmol), M9 (0.2 g, 0.85 mmol) and chloroform (CF, 15 mL) were placed into a 100 mL three-neck reaction flask and stirred. The reaction was deoxygenated with argon for 30 minutes. Pyridine (0.3 mL) was added. After reacting for 1 hour, methanol was added to precipitate the product. The reaction mixture was suction filtered to obtain the product A2 as a dark blue solid (240 mg, yield 58%). $^1$H NMR (500 MHz, $CDCl_3$): δ 8.77 (s, 2H), 8.63 (m, 2H), 8.53 (d, J=12.0 Hz, 2H), 7.93 (s, 2H), 7.75 (d, J=14.0 Hz, 2H), 4.66-4.63 (m, 4H), 3.05-3.02 (m, 4H), 2.09-2.08 (m, 2H), 1.87 (m, 4H), 1.49-1.25 (m, 96H), 0.87-0.68 (m, 18H).

An acceptor material A2-1 of an active layer material synthesized from M1:

Synthesis of M5-1:

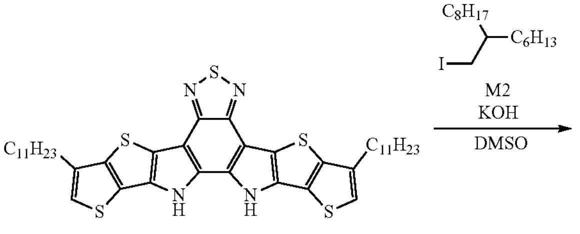

M1

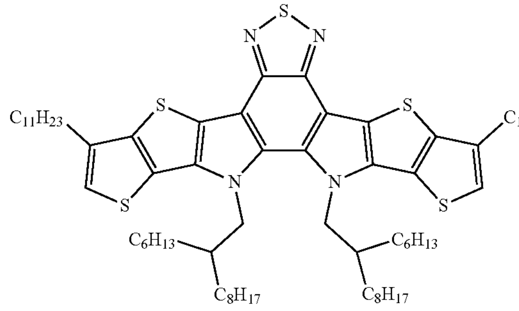

M5-1

M1 (1.0 g, 1.3 mmol), and potassium hydroxide (KOH, 0.2 g, 4.0 mmol) were placed into a 100 mL three-neck reaction flask. Dimethyl sulfoxide (DMSO, 30 mL) was added, and the reaction mixture was stirred at room temperature for 30 minutes. 1-Iodo-2-hexyldodecane (1.8 g, 5.4 mmol) was added at room temperature. The temperature was raised to 80 °C for 18 hours. The reaction was cooled to room temperature and extracted three times with ethyl acetate/water. The organic layer was collected and was dried with magnesium sulfate, and the solvent was removed. The crude product was purified by a silica gel column (eluent: heptane/dichloromethane=3/1) to obtain the product M5-1 as a red solid (1.2 g, yield 77%). $^1$H NMR (500 MHz, $CDCl_3$): δ 7.01 (s, 2H), 4.59 (d, J=8.0 Hz, 4H), 2.82 (t, J=7.8 Hz, 4H), 2.08-2.05 (m, 2H), 1.87-1.84 (m, 4H), 1.45-0.97 (m, 80H), 0.99-0.66 (d, J=7.0 Hz, 18H).

Synthesis of M6-1:

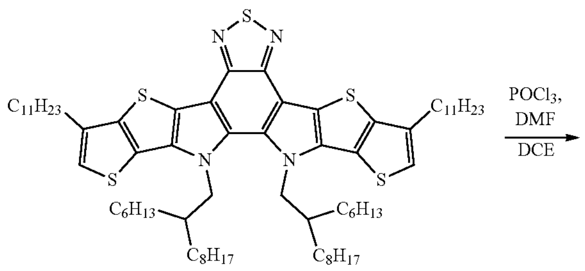

M5

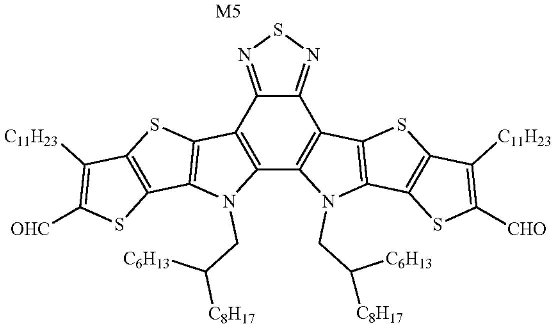

M6-1

In an ice bath, phosphorus oxychloride ($POCl_3$, 0.9 g, 6.0 mmol) and dimethylformamide (DMF, 3.7 g, 50.2 mmol) were mixed in a 100 mL three-necked reaction flask and stirred for 30 minutes to form a Vilsmeier reagent. M5-1 (1.2 g, 1.0 mmol) was placed into another 100 mL three-necked reaction flask. Dichloroethane (DCE, 60 mL) was added and stirred, then the Vilsmeier reagent was injected in. The reaction was heated to 60 °C for 18 hours. The reaction was cooled to room temperature and extracted three times with dichloromethane/water. The organic layer was collected and was dried with magnesium sulfate, and the solvent was removed. The crude product was purified by a silica gel column (eluent: heptane/dichloromethane=1/1) to obtain the product M6-1 as a red solid (1.1 g, yield 90%). $^1$H NMR (500 MHz, $CDCl_3$): δ 10.14 (s, 2H), 4.62 (d, J=8.0 Hz, 4H), 3.20 (t, J=7.5 Hz, 4H), 2.02 (m, 2H), 1.93 (m, 4H), 1.48-0.94 (m, 80H), 0.91-0.66 (m, 18H).

Synthesis of M8-1:

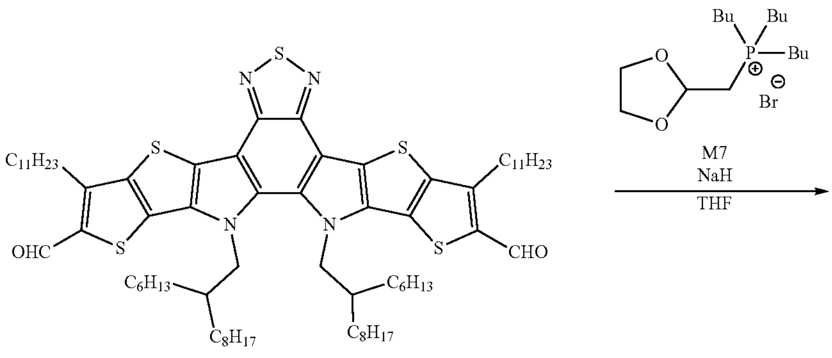

M6-1

-continued

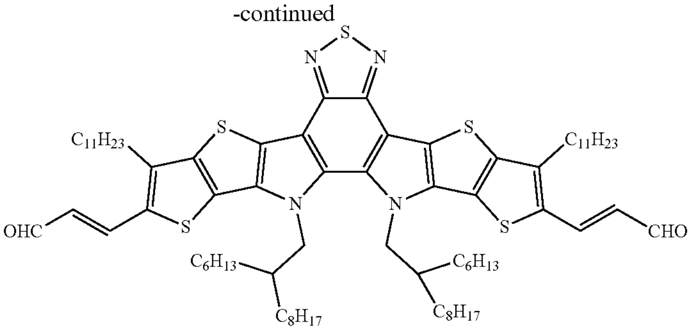

M8-1

M6-1 (1.1 g, 0.9 mmol), M7 (1.3 g, 3.5 mmol), and sodium hydride (NaH, 0.13 g, 5.3 mmol) were mixed in a 100 mL three-necked reaction flask. Anhydrous tetrahydrofuran (THF, 55 mL) was added and the reaction was stirred for 18 hours. In an ice bath, dilute hydrochloric acid (10%, 5.5 mL) was added and reacted for 30 minutes. The reaction was extracted three times with ethyl acetate/water. The organic layer was collected and was dried with magnesium sulfate, and the solvent was removed. The crude product was purified by a silica gel column (eluent: heptane/dichloromethane=1/1) to obtain the product M8-1 as a red solid (1.1 g, yield 92%). $^1H$ NMR (500 MHz, $CDCl_3$): δ 9.70 (d, J=7.5 Hz, 2H), 7.78 (d, J=15.0 Hz, 2H), 6.52 (dd, $J^1$=15.0 Hz, $J^2$=7.5 Hz, 2H), 4.59 (d, J=7.5 Hz, 4H), 2.99 (t, J=7.8 Hz, 4H), 2.03 (m, 2H), 1.87-1.85 (m, 4H), 1.49-0.92 (m, 80H), 0.89-0.67 (m, 18H).

Synthesis of A2-1:

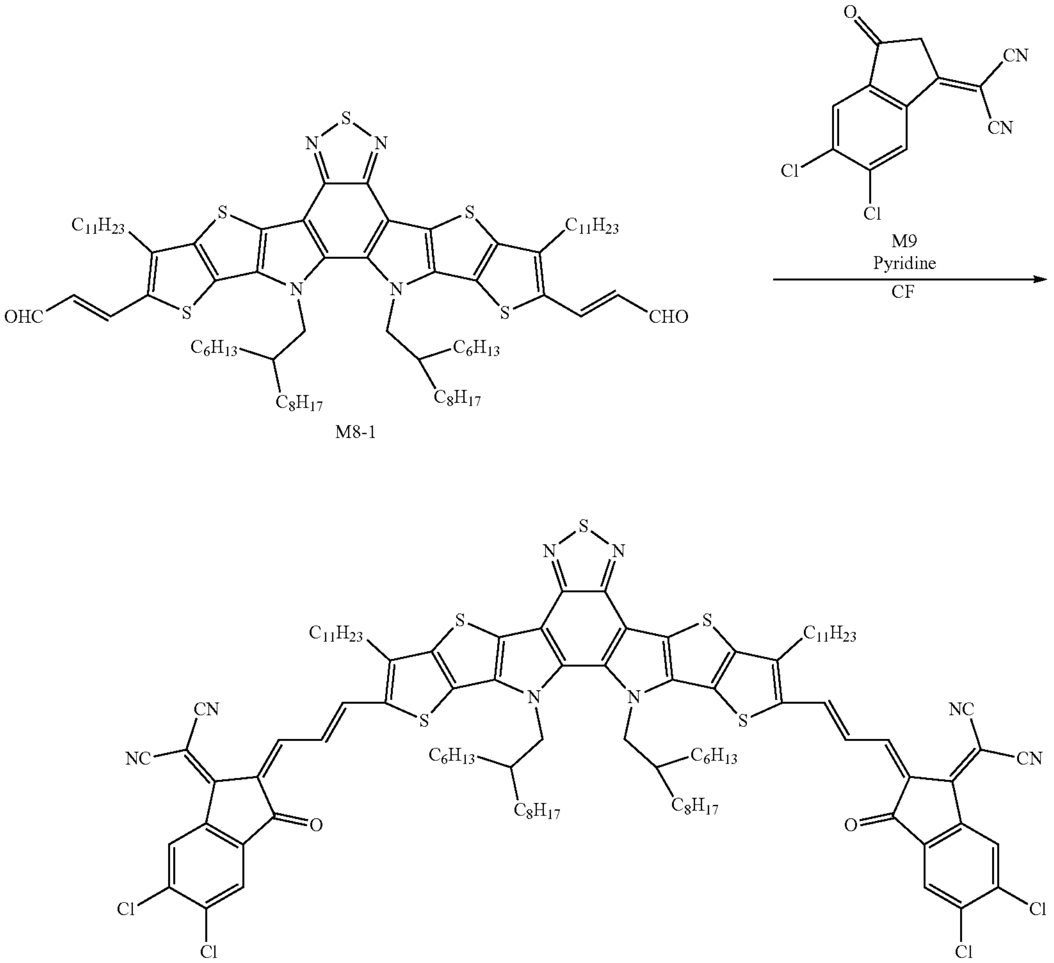

M8-1

A2-1

M8-1 (0.3 g, 0.23 mmol), M9 (0.2 g, 0.92 mmol) and chloroform (15 mL) were placed into a 100 mL three-neck reaction flask and stirred. The reaction was deoxygenated with argon for 30 minutes. Pyridine (0.3 mL) was added. After reacting for 1 hour, methanol was added to precipitate the product. The reaction mixture was suction filtered to obtain the product A2-1 as a dark blue solid (260 mg, yield 63%). $^1$H NMR (500 MHz, $CDCl_3$): δ 8.78 (s, 2H), 8.62 (m, 2H), 8.55 (m, 2H), 7.94 (s, 2H), 7.77 (m, 2H), 4.73 (m, 4H), 3.04 (m, 4H), 2.15 (m, 2H), 1.85 (m, 4H), 1.27-0.98 (m, 80H), 0.88-0.68 (m, 18H).

An acceptor material A2-2 of an active layer material synthesized from M1:

Synthesis of M5-2:

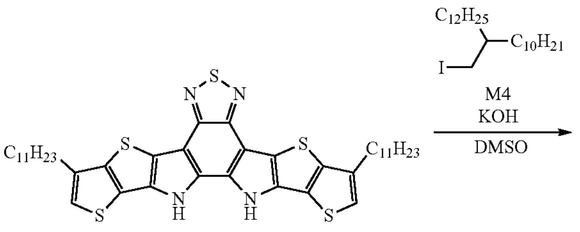

M1

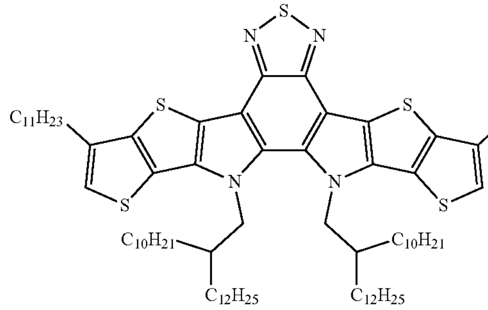
M5-2

M1 (1.0 g, 1.3 mmol), and potassium hydroxide (KOH, 0.2 g, 4.0 mmol) were placed into a 100 mL three-neck reaction flask. Dimethyl sulfoxide (DMSO, 21 mL) was added, and the reaction mixture was stirred at room temperature for 30 minutes, and then 1-iodo-2-decyltetradecane (2.5 g, 5.4 mmol) was added at room temperature. The temperature was raised to 80 °C for 18 hours. The reaction was cooled to room temperature and extracted three times with ethyl acetate/water (EA/$H_2O$). The organic layer was collected and was dried with magnesium sulfate, and the solvent was removed. The crude product was purified by a silica gel column (eluent: heptane/dichloromethane=3/1) to obtain the product M5-2 as a red solid (1.4 g, yield 75%). $^1$H NMR (500 MHz, $CDCl_3$): δ 7.00 (s, 2H), 4.58 (d, J=8.0 Hz, 4H), 2.81 (t, J=7.8 Hz, 4H), 2.07-2.05 (m, 2H), 1.89-1.83 (m, 4H), 1.48-0.90 (m, 112H), 0.87-0.66 (m, 18H).

Synthesis of M6-2:

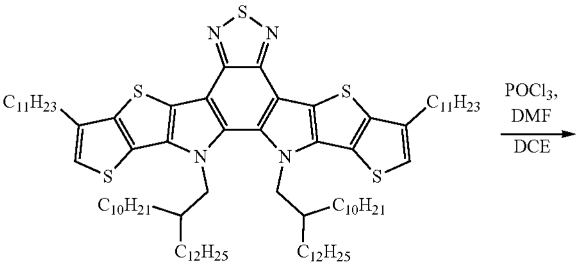

M5-2

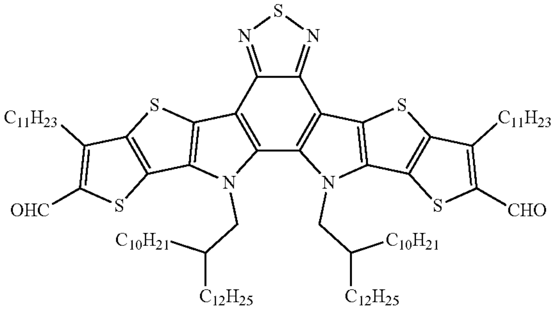
M6-2

In an ice bath, phosphorus oxychloride ($POCl_3$, 0.9 g, 5.9 mmol) and dimethylformamide (DMF, 3.6 g, 49.3 mmol) were mixed in a 100 mL three-necked reaction flask and stirred for 30 minutes to form a Vilsmeier reagent. M5-2 (1.4 g, 1.0 mmol) was placed into another 100 mL three-necked reaction flask. Dichloroethane (DCE, 70 mL) was added and stirred, then the Vilsmeier reagent was injected in. The reaction was heated to 60 °C for 18 hours. The reaction was cooled to room temperature and extracted three times with dichloromethane/water. The organic layer was collected and was dried with magnesium sulfate, and the solvent was removed. The crude product was purified by a silica gel column (eluent: heptane/dichloromethane=1/1) to obtain the product M6-2 as a red solid (1.3 g, yield 88%). $^1$H NMR (500 MHz, $CDCl_3$): δ 10.14 (s, 2H), 4.62 (d, J=8.0 Hz, 4H), 3.20 (t, J=7.8 Hz, 4H), 2.03 (m, 2H), 1.95-1.84 (m, 4H), 1.50-0.96 (m, 112H), 0.66 (d, J=7.0 Hz, 18H).

Synthesis of M8-2:

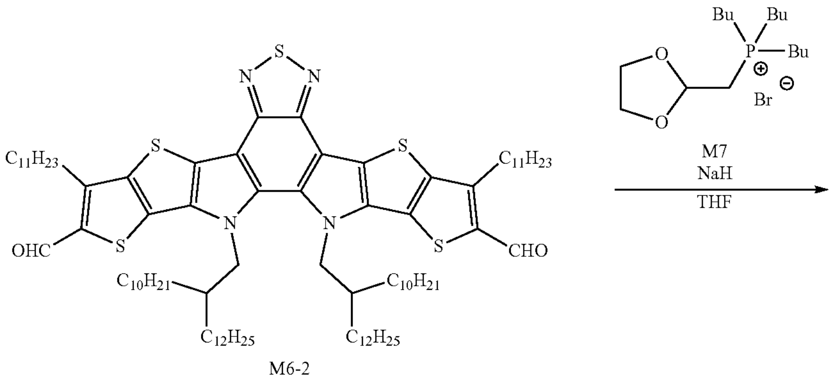

M6-2

-continued

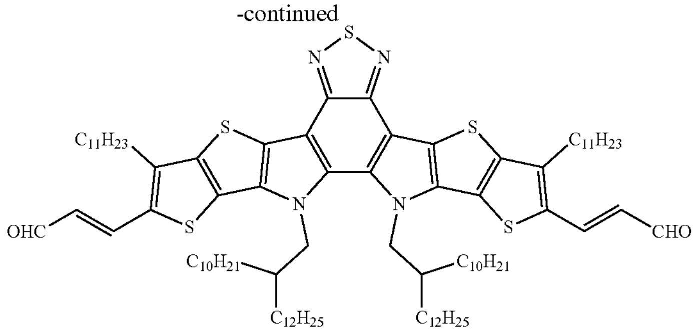

M8-2

M6-2 (1.3 g, 0.9 mmol), M7 (1.3 g, 3.5 mmol), and sodium hydride (NaH, 0.13 g, 5.3 mmol) were mixed in a 100 mL three-necked reaction flask. Anhydrous tetrahydrofuran (THF, 39 mL) was added and the reaction was stirred for 18 hours. In an ice bath, dilute hydrochloric acid (10%, 6.5 mL) was added and reacted for 30 minutes. The reaction was extracted three times with ethyl acetate/water. The organic layer was collected and was dried with magnesium sulfate, and the solvent was removed. The crude product was purified by a silica gel column (eluent: heptane/dichloromethane=1/1) to obtain the product M8-2 as a red solid (1.3 g, yield 95%). $^1H$ NMR (500 MHz, $CDCl_3$): δ 9.70 (d, J=7.5 Hz, 2H), 7.77 (d, J=15.0 Hz, 2H), 6.52 (dd, $J^1$=15.0 Hz, $J^2$=7.5 Hz, 2H), 4.59 (d, J=8.0 Hz, 4H), 2.99 (t, J=7.8 Hz, 4H), 2.03-2.01 (m, 2H), 1.89-1.83 (m, 4H), 1.49-0.92 (m, 112H), 0.89-0.66 (m, 18H).

Synthesis of A2-2:

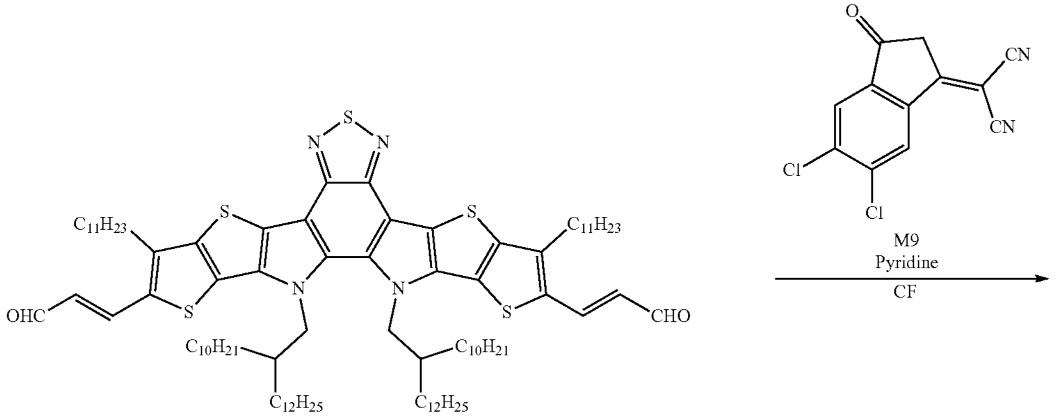

M8-2

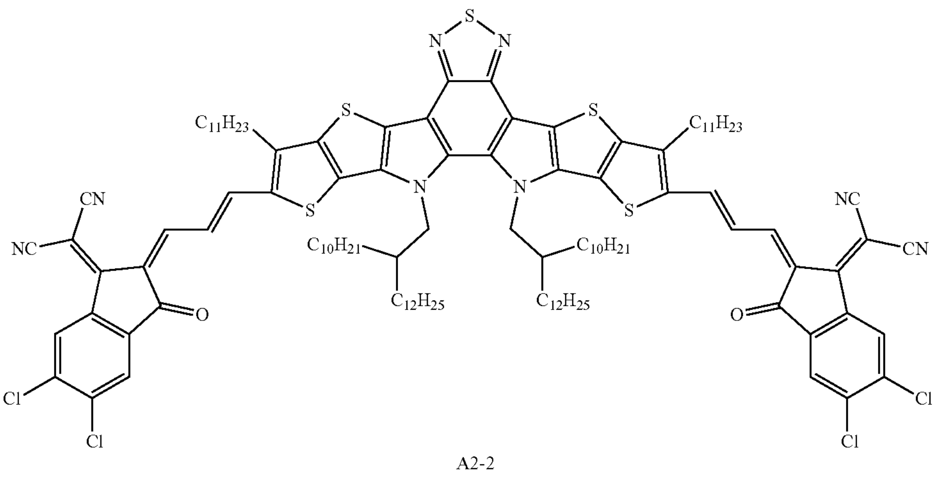

A2-2

M8-2 (0.3 g, 0.20 mmol), M9 (0.2 g, 0.79 mmol) and chloroform (CF, 15 mL) were placed into a 100 mL three-neck reaction flask and stirred. The reaction was deoxygenated with argon for 30 minutes. Pyridine (0.3 mL) was added. After reacting for 1 hour, methanol was added to precipitate the product. The reaction mixture was suction filtered to obtain the product A2-2 as a dark blue solid (250 mg, yield 63%). $^1$H NMR (500 MHz, $CDCl_3$): δ 8.78 (s, 2H), 8.67-8.64 (m, 2H), 8.54 (d, J=12.0 Hz, 2H), 7.94 (s, 2H), 7.75 (d, J=14.0 Hz, 2H), 4.63 (d, J=7.5 Hz, 4H), 3.03 (t, J=7.8 Hz, 4H), 2.08 (m, 2H), 1.90-1.84 (m, 4H), 1.51-0.97 (m, 112H), 0.88-0.68 (m, 18H).

An acceptor material mixture A2 of an active layer material synthesized from M1:

Synthesis of Mixture 1:

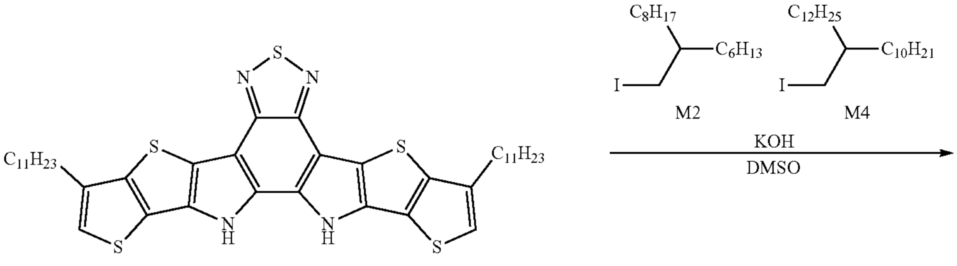

M1 M2 M4

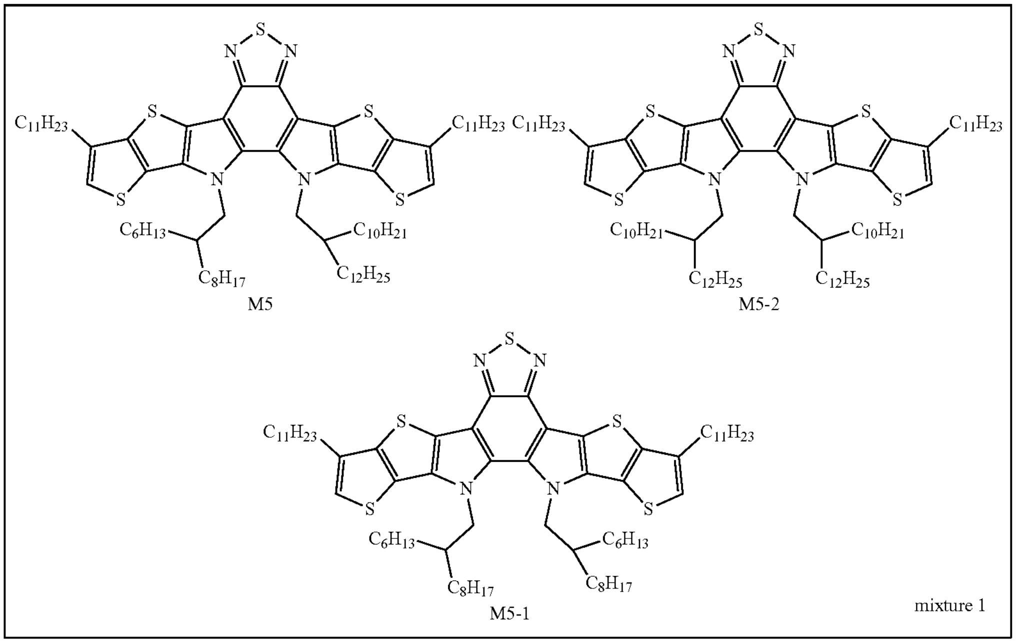

M5 M5-2 M5-1 mixture 1

M1 (1.0 g, 1.3 mmol), and potassium hydroxide (KOH, 0.4 g, 7.8 mmol) were placed into a 100 mL three-neck reaction flask. Dimethyl sulfoxide (DMSO, 30 mL) was added, and the reaction mixture was stirred at room temperature for 30 minutes. 1-Iodo-2-decyltetradecane (2.8 g, 6.0 mmol) and 1-iodo-2-hexyldodecane (2.1 g, 6.0 mmol) was added. The temperature was raised to 80 °C for 18 hours. The reaction was cooled to room temperature and extracted three times with ethyl acetate/water. The organic layer was collected and was dried with magnesium sulfate, and the solvent was removed. The crude product was purified by a silica gel column (eluent: heptane/dichloromethane=3/1) to obtain the product mixture 1 (1.2 g, yield 74%). Mixture 1 comprises M5, M5-1 and M5-2. Individual content was analyzed by high performance liquid chromatography. In the aforementioned synthesis, the retention times of three different products were identified and confirmed respectively, M5 was 14.33 minutes, M5-1 was 10.14 minutes, and M5-2 was 20.78 minutes. Based on this analysis, it can be known that the proportion of each component in mixture 1: M5 was 47%, M5-1 was 36%, and M5-2 was 17%.

Synthesis of Mixture 2:

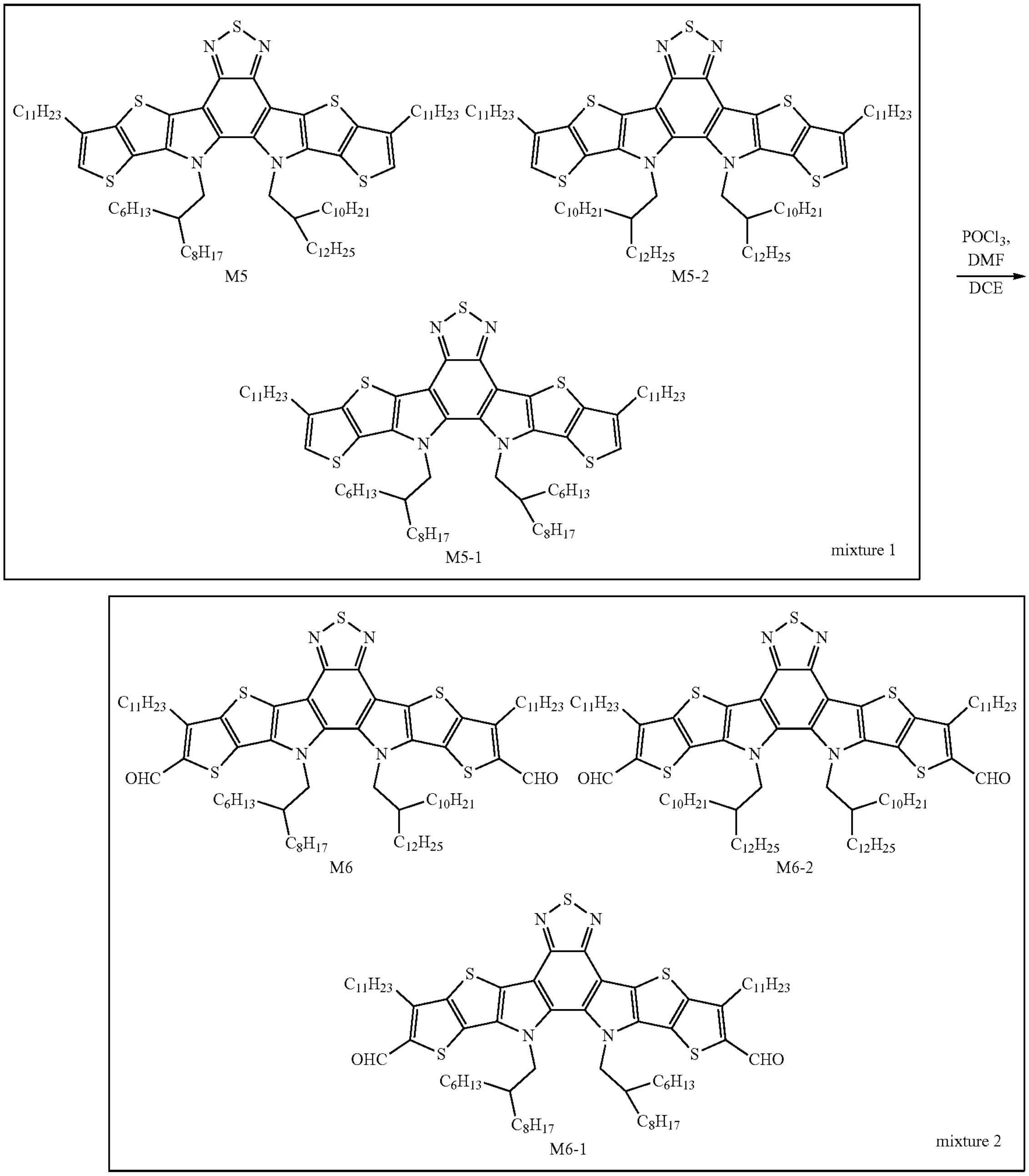

M5 M5-2 M5-1 mixture 1

M6 M6-2 M6-1 mixture 2

In an ice bath, phosphorus oxychloride ($POCl_3$, 0.8 g) and dimethylformamide (DMF, 3.6 g) were mixed in a 100 mL three-necked reaction flask and stirred for 30 minutes to form a Vilsmeier reagent. Mixture 1 (1.2 g) was placed into another 100 mL three-necked reaction flask. Dichloroethane (DCE, 60 mL) was added and stirred, then the Vilsmeier reagent was injected in. The reaction was heated to 60 °C for 18 hours. The reaction was cooled to room temperature and extracted three times with dichloromethane/water. The organic layer was collected and was dried with magnesium sulfate, and the solvent was removed. The crude product was purified by a silica gel column (eluent: heptane/dichloromethane=1/1) to obtain the product mixture 2 (1.3 g, yield 93%). Mixture 2 comprises M6, M6-1 and M6-2. Individual content was analyzed by high performance liquid chromatography. In the aforementioned synthesis, the retention times of three different products were identified and confirmed respectively, M6 was 9.76 minutes, M6-1 was 7.23 minutes, and M6-2 was 13.57 minutes. Based on this analysis, it can be known that the proportion of each component in mixture 2: M6 is 48%, M6-1 is 36%, and M6-2 is 16%.

Synthesis of Mixture 3:

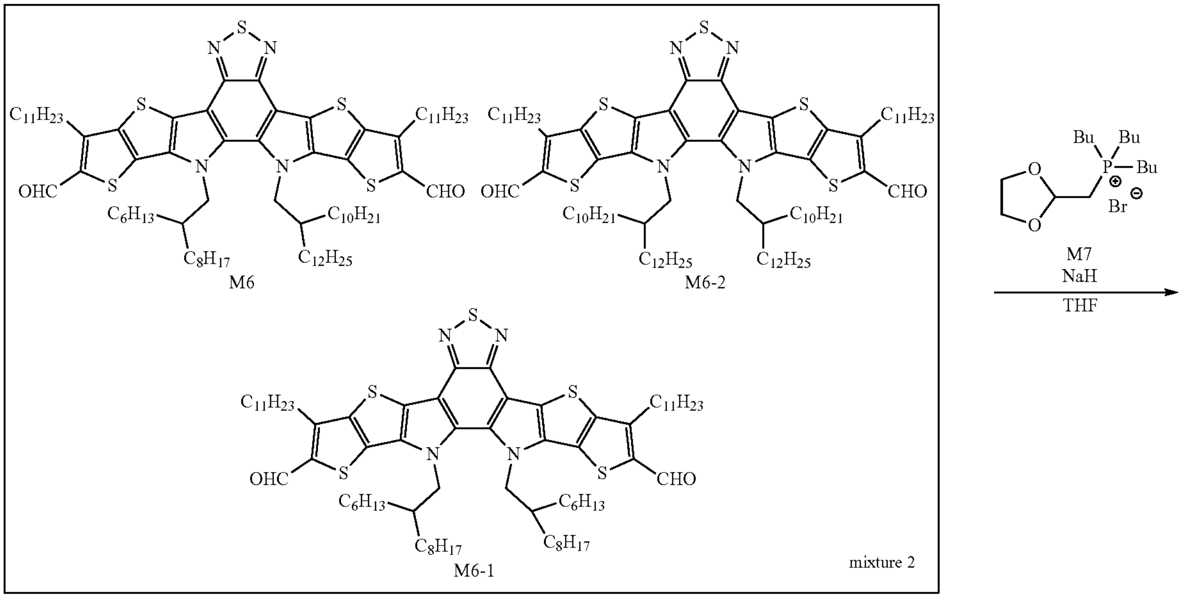

M6 M6-2 M6-1 mixture 2

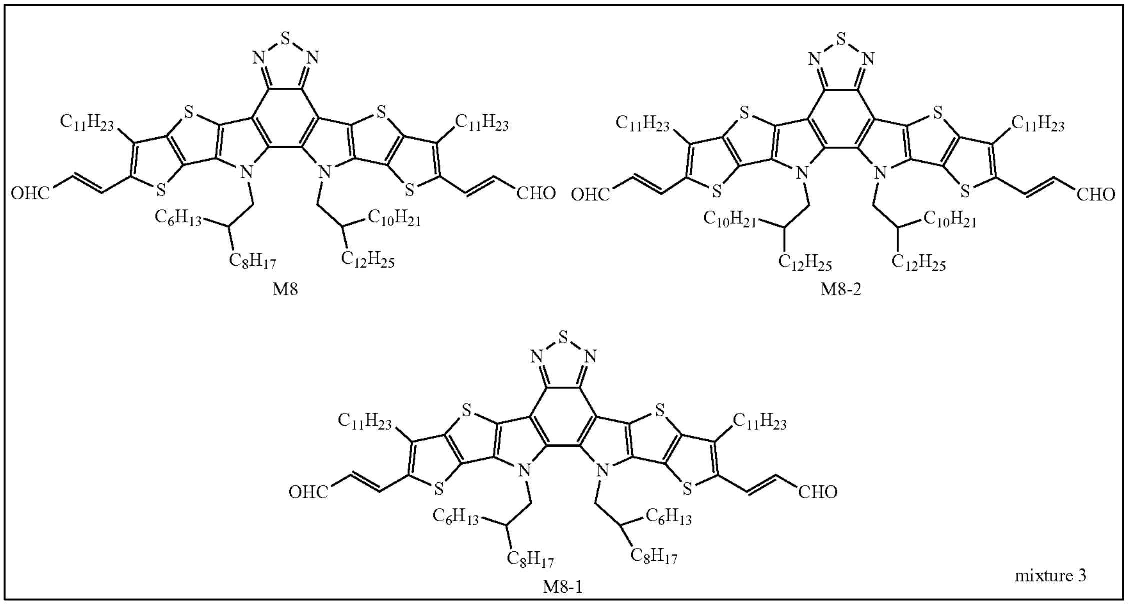

M8 M8-2 M8-1 mixture 3

Mixture 2 (1.3 g), M7 (1.3 g), and sodium hydride (NaH, 0.13 g) were mixed in a 100 mL three-necked reaction flask. Anhydrous tetrahydrofuran (THF, 39 mL) was added and the reaction was stirred for 18 hours. In an ice bath, dilute hydrochloric acid (10%, 6.5 mL) was added and reacted for 30 minutes. The reaction was extracted three times with ethyl acetate/water. The organic layer was collected and was dried with magnesium sulfate, and the solvent was removed. The crude product was purified by a silica gel column (eluent: heptane/dichloromethane=1/1) to obtain the product mixture 3 (1.2 g, yield 96%). Mixture 3 comprises M8, M8-1 and M8-2. Individual content was analyzed by high performance liquid chromatography. In the aforementioned synthesis, the retention times of three different products were identified and confirmed respectively, M8 was 8.27 minutes, M8-1 was 6.36 minutes, and M8-2 was 11.05 minutes. Based on this analysis, it can be known that the proportion of each component in mixture 3: M8 is 47%, M8-1 is 37%, and M8-2 is 16%.

Synthesis of Mixture A2:

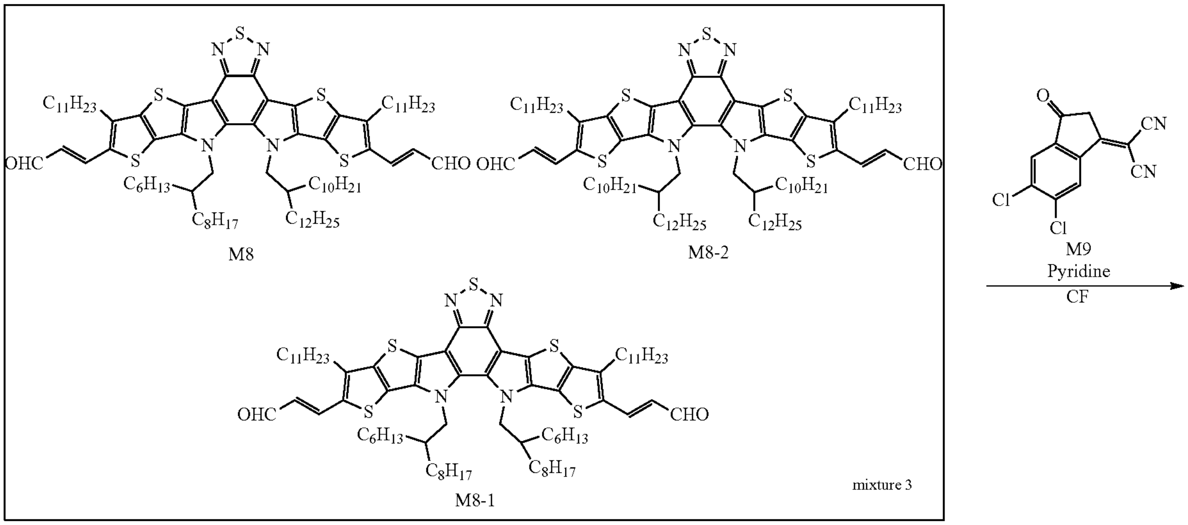

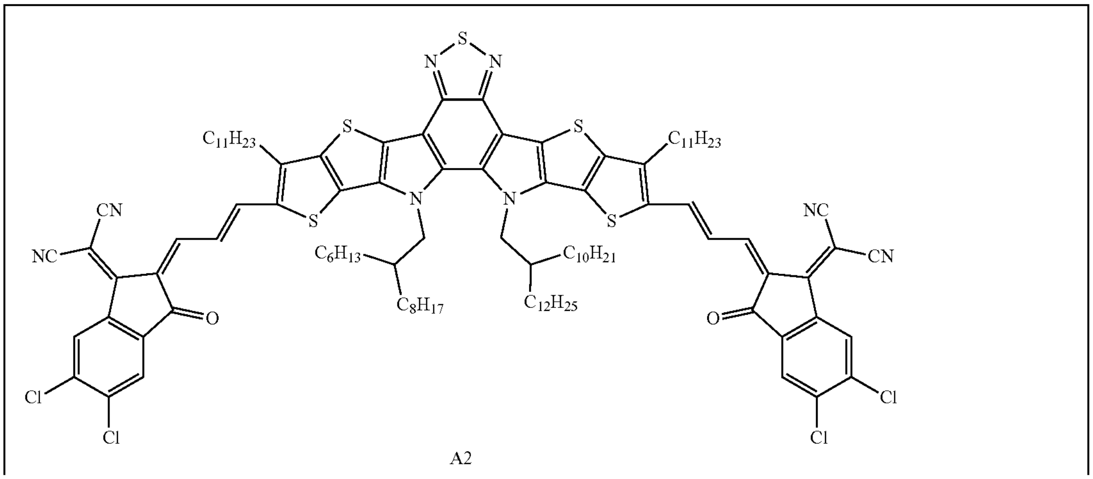

-continued

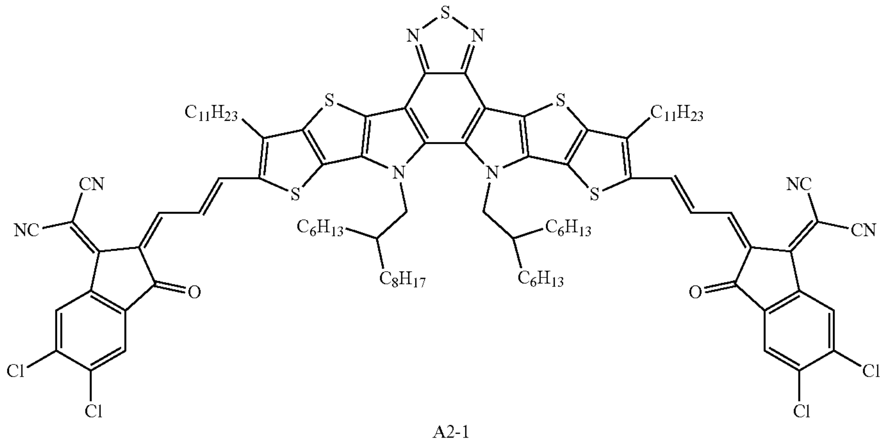

A2-1

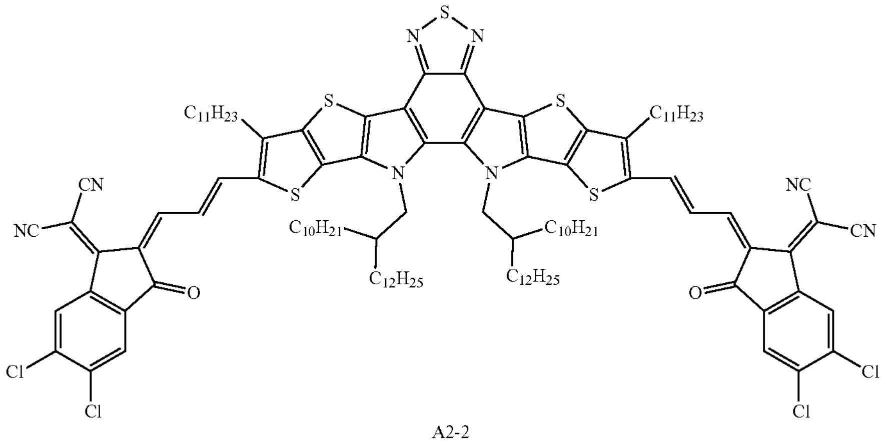

A2-2 mixture A2

Mixture 3 (250 mg), M9 (0.2 g) and chloroform (CF, 15 mL) were placed into a 100 mL three-neck reaction flask and stirred. The reaction was deoxygenated with argon for 30 minutes. Pyridine (0.3 mL) was added. After reacting for 1 hour, methanol was added to precipitate the product. The reaction mixture was suction filtered to obtain the product mixture A2 as a dark blue solid (240 mg, yield 71%). Mixture A2 comprises A2, A2-1 and A2-2. Individual content was analyzed by high performance liquid chromatography. In the aforementioned synthesis, the retention times of three different products were identified and confirmed respectively, A2 was 13.42 minutes, A2-1 was 9.91 minutes, and A2-2 was 18.25 minutes. Based on this analysis, it can be known that the proportion of each component in mixture A2: A2 is 48%, A2-1 is 36%, and A2-2 is 16%.

The present invention develops a synthesis method of a mixture (as listed in the above synthesis steps), from M1 to mixture A2. Wherein, mixture 1, mixture 2, mixture 3 and mixture A2 all contain three compounds. The proportion of each compound in each mixture was identified by high performance liquid chromatography. As listed in Table 1, Table 1 shows the ratio of each compound in each mixture.

TABLE 1

Proportion of each compound in each mixture

| Mixture combination | Mixture ratio M5 | M5-1 | M5-2 |
|---|---|---|---|
| mixture 1 | 47% | 36% | 17% |
| | M6 | M6-1 | M6-2 |
| mixture 2 | 48% | 36% | 16% |
| | M8 | M8-1 | M8-2 |
| mixture 3 | 47% | 37% | 16% |
| | A2 | A2-1 | A2-2 |
| mixture A2 | 48% | 36% | 16% |

It can be seen from Table 1 that after four synthesis steps from M1, the proportions of the three compounds are similar. Wherein, the mixture ratios of M5, M6, M8 and A2 are all between 47% and 48%, the mixture ratios of M5-1, M6-1, M8-1 and A2-1 are all between 36% and 37%, and the mixture ratios of M5-2 and M6-2, M8-2 and A2-2 are all between 16-17%. It can be seen that the synthesis method of the mixture of the present invention has good synthesis stability.

Figure 2:
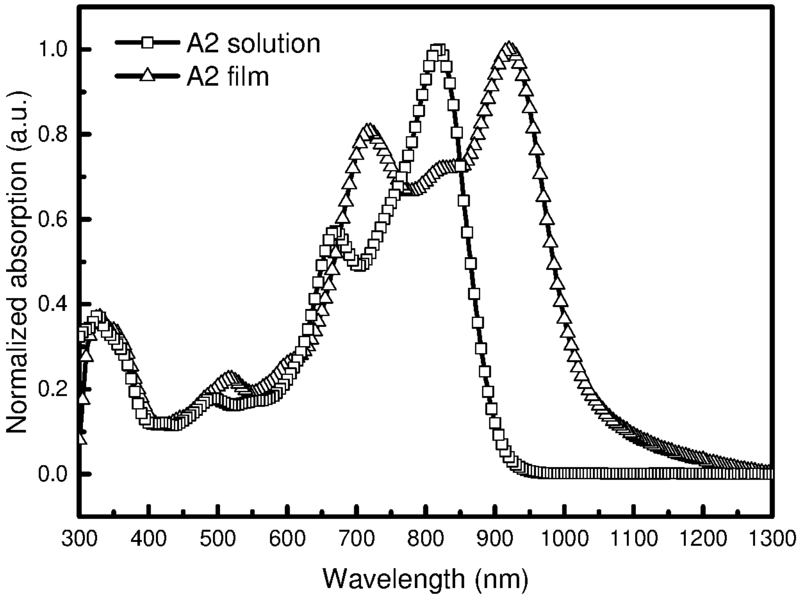
FIG. 2 shows an absorption spectrum of an embodiment A2 of the near-infrared organic small molecule with vinyl groups of the present invention in solution state and thin film state.
Figure 3:
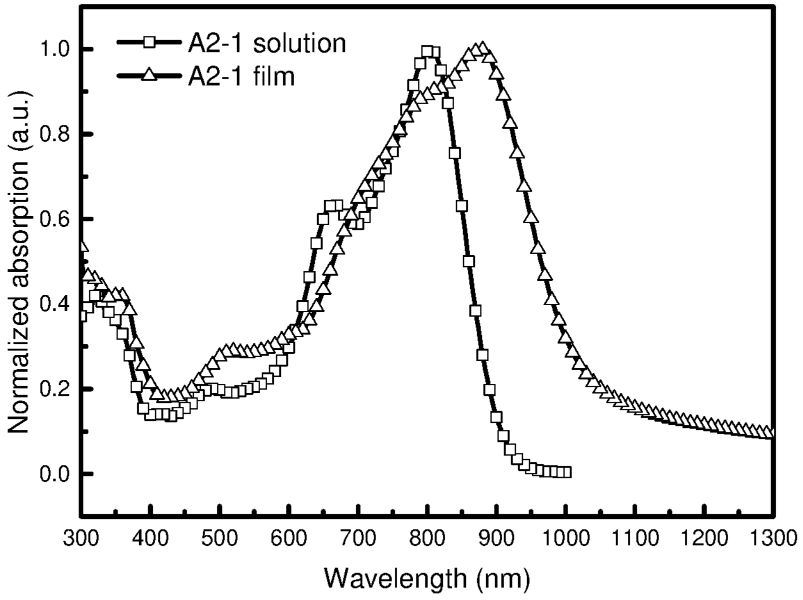
FIG. 3 shows an absorption spectrum of an embodiment A2-1 of the near-infrared organic small molecule with vinyl groups of the present invention in solution state and thin film state.
Figure 4:
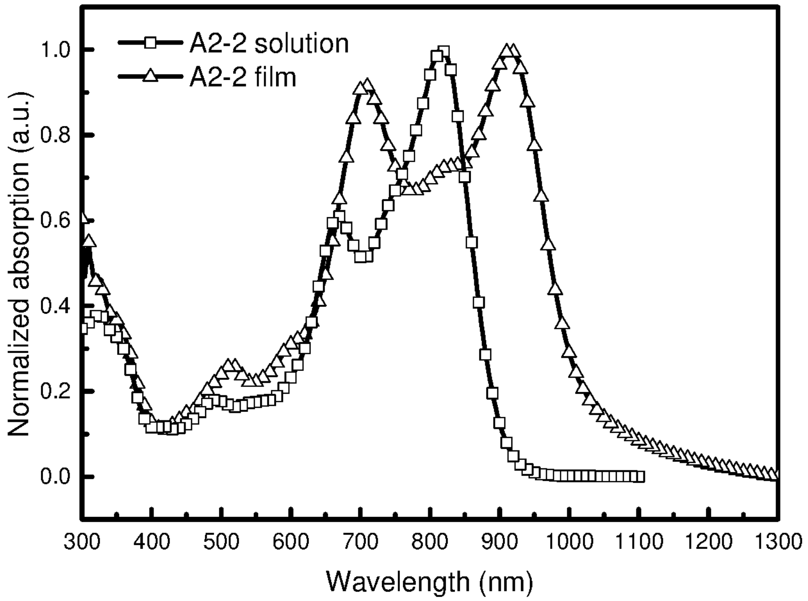
FIG. 4 shows an absorption spectrum of an embodiment A2-2 of the near-infrared organic small molecule with vinyl groups of the present invention in solution state and thin film state.
Figure 5:
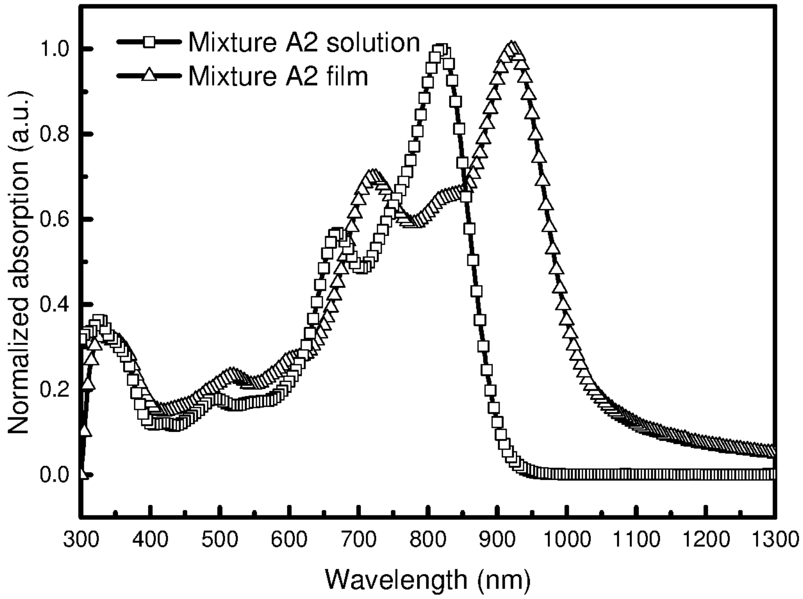
FIG. 5 shows an absorption spectrum of an embodiment mixture A2 of the near-infrared organic small molecule with vinyl groups of the present invention in solution state and thin film state.

Material Performance Test of Near-Infrared Organic Small Molecules with Vinyl Groups A2 to Mixture A2 includes Material Optical Properties and Electrochemical Properties:

Please refer to FIG. 2 to FIG. 5 and Table 2. FIG. 2 shows an absorption spectrum of an embodiments A2 of the near-infrared organic small molecule with vinyl groups of the present invention in solution state and thin film state. FIG. 3 shows an absorption spectrum of an embodiments A2-1 of the near-infrared organic small molecule with vinyl groups of the present invention in solution state and thin film state. FIG. 4 shows an absorption spectrum of an embodiments A2-2 of the near-infrared organic small molecule with vinyl groups of the present invention in solution state and thin film state. FIG. 5 shows an absorption spectrum of an embodiment mixture A2 of the near-infrared organic small molecule with vinyl groups of the present invention in solution state and thin film state. Table 2 shows the data results from FIG. 2 to FIG. 5.

TABLE 2

Data results from FIG. 2 to FIG. 5

| | $\lambda_{soln}^{max}$ (nm) | $\lambda_{film}^{max}$ (nm) | $\lambda_{film}^{onset}$ (nm) | ε ($10^5$ $cm^{-1}M^{-1}$) | $E_g^{opt}$ (eV) | HOMO (eV) | LUMO (eV) |
|---|---|---|---|---|---|---|---|
| A2 | 818 | 922 | 1012 | 1.14 | 1.23 | −5.59 | −4.36 |
| A2-1 | 804 | 870 | 1002 | 0.94 | 1.24 | −5.54 | −4.30 |
| A2-2 | 814 | 914 | 1016 | 1.21 | 1.22 | −5.67 | −4.45 |
| Mixture A2 | 820 | 924 | 1020 | 1.14 | 1.22 | −5.54 | −4.32 |

As shown in FIG. 2 and Table 2, A2 has a good performance in the absorption spectrum. The maximum absorption value of its thin film state is at 922 nm, and the onset value of absorption is at 1012 nm. Therefore, it can be seen from the thin film state absorption spectrum that A2 has good absorption properties in the range of 900~1000 nm, and its optical properties conform to the target responsibility of 900~1000 nm designed by the present invention. As shown in FIG. 3, FIG. 4 and Table 2, the absorption spectra of comparative examples A2-1 and A2-2 also have good absorption properties at 900~1000 nm. As shown in FIG. 5 and Table 2, mixture A2 obtained by mixing A2, A2-1 and A2-2 in specific proportions also maintains good optical properties through the preparation process of mixture A2 of the present invention.

Film Surface Quality Test:

Prepare the active layer solution in o-xylene (weight ratio of donor:acceptor is 1:1-2). The concentration of donor material was 20 mg/mL. In order to completely dissolve the polymer, the active layer solution should be stirred on a hot plate at 100 °C for at least 3 hours. After cooling down to room temperature, filter it with a PTFE filter membrane (pore size 0.45~1.2 μm). Next, the active layer solution is heated for 1 hour. Then, the solution is cooled at room temperature and then coated, and the film thickness is controlled to be in the range of 100~200 nm by the spin rate. The active layer film was annealed at 100 °C for 5 minutes. The state of the film surface was observed with an optical microscope (magnification: 50×). It needs to be understood is that the above are the experimental parameters of the film surface test, and the experimental parameters can be adjusted according to the actual situation, and are not limited to this.

Figure 6:
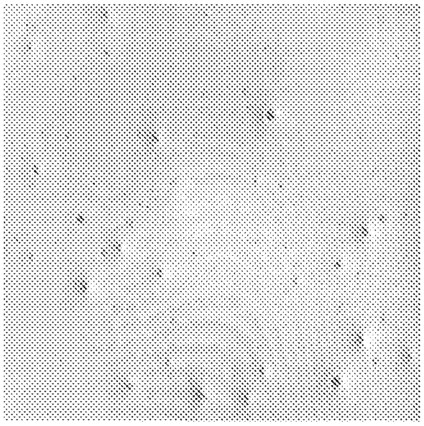
FIG. 6 shows the film surface quality test results of comparative example 1 of the active layer material of the present invention.
Figure 9:
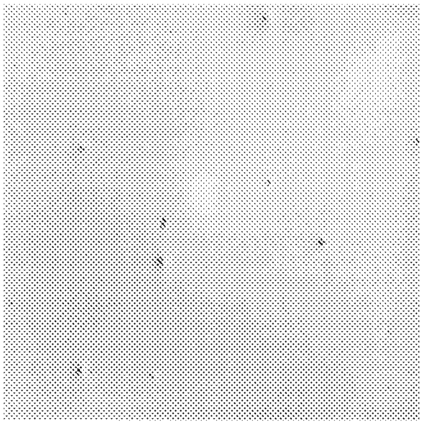
FIG. 9 shows the film surface quality test results of comparative example 4 of the active layer material of the present invention.
Figure 7:
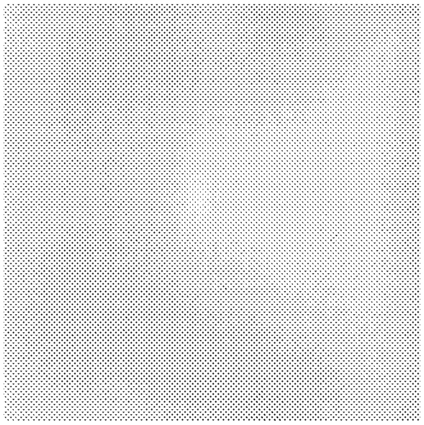
FIG. 7 shows the film surface quality test results of comparative example 2 of the active layer material of the present invention.
Figure 10:
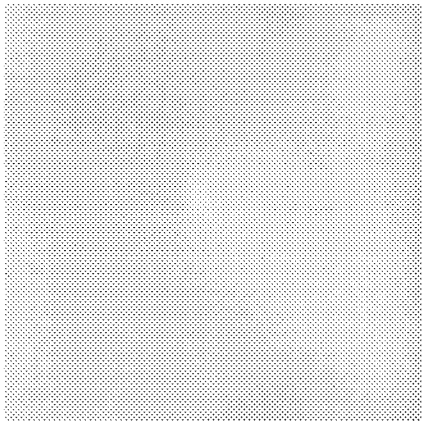
FIG. 10 shows the film surface quality test results of example 1 of the active layer material of the present invention.
Figure 8:
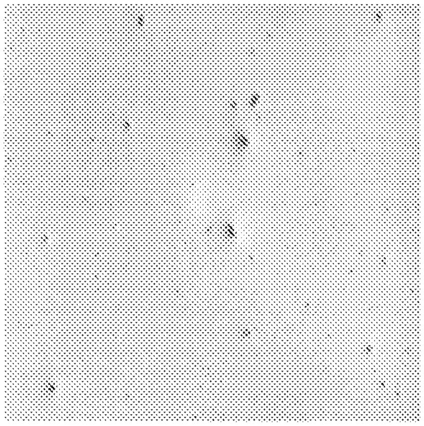
FIG. 8 shows the film surface quality test results of comparative example 3 of the active layer material of the present invention.
Figure 11:
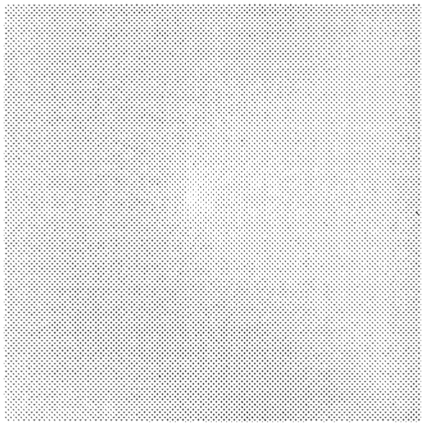
FIG. 11 shows the film surface quality test results of example 2 of the active layer material of the present invention.

Please refer to FIG. 6 to FIG. 11 and Table 3. FIG. 6 shows the film surface quality test results of comparative example 1 of the active layer material of the present invention. FIG. 7 shows the film surface quality test results of comparative example 2 of the active layer material of the present invention. FIG. 8 shows the film surface quality test results of comparative example 3 of the active layer material of the present invention. FIG. 9 shows the film surface quality test results of comparative example 4 of the active layer material of the present invention. FIG. 10 shows the film surface quality test results of example 1 of the active layer material of the present invention. FIG. 11 shows the film surface quality test results of example 2 of the active layer material of the present invention. Table 3 shows the composition ratio of each active layer material.

TABLE 3

The composition ratio of each active layer material

| Active layer material | Donor material | The ratio of acceptor material A2 | A2-1 | A2-2 |
|---|---|---|---|---|
| comparative example 1 | Polymer 14 | 0 | 1 | 0 |
| comparative example 2 | Polymer 14 | 0 | 0 | 1 |
| comparative example 3 | Polymer 14 | 0 | 2 | 1 |

TABLE 3-continued

| The composition ratio of each active layer material | | | | |
|---|---|---|---|---|
| comparative example 4 | Polymer 14 | 0 | 1.4 | 1 |
| example 1 | Polymer 14 | 1 | 0 | 0 |
| | | | mixture A2 | |
| example 2 | Polymer 14 | 48 | 36 | 16 |

| Active layer material | Donor material | Acceptor material |
|---|---|---|
| reference example 1 | Polymer 9 | CO1-4Cl |

As shown in Table 3, in this test, polymer 14 is used as the donor material in the active layer materials. Comparative example 1 contains only A2-1, comparative example 2 contains only A2-2, example 1 contains only A2, and example 2 contains mixture A2. In addition, mix A2-1 and A2-2 in different proportions to further explore the influence of A2 in the combination. Wherein, comparative example 3 was prepared with A2-1:A2-2=2:1, and comparative example 4 was prepared with A2-1:A2-2=1.4:1. When testing the six groups of active layer materials, as shown in FIG. 6 to FIG. 11, the film surface quality of comparative examples 1, 3, and 4 are not good during film formation. The main reason is that the acceptor material A2-1 has strong crystallinity which results in aggregation when blending with polymer 14. Even with different proportions of the acceptor material A2-2, the problem of film surface cannot be solved. For the other three groups of the active layer materials, the film surfaces of comparative example 2, example 1, and example 2 are smooth. The main reason is that the acceptor material A2-2 and the acceptor material A2 have more long carbon chains, and they can effectively alleviate the problem of material crystallinity. Moreover, mixture A2 of A2, A2-1 and A2-2 can also alleviate the crystallinity of A2-1 due to the addition of A2 and A2-2, and form a good film surface.

Preparation and Performance Testing of Organic Photodetector Devices of Organic Optoelectronic Devices:

A glass coated by a pre-patterned indium tin oxide (ITO) with a sheet resistance of ~15 Ω/sq is used as a substrate. The substrate is ultrasonically oscillated in soap deionized water, deionized water, acetone, and isopropanol in sequence, and washed in each step for 15 minutes. The washed substrate is further treated with a UV-ozone cleaner for 30 minutes. The top coat of AZO (Aluminum-doped zinc oxide) solution is spin coated on the ITO substrate with a spin rate of 2000 rpm for 40 seconds, and then baked at 120 °C in air for 5 minutes to form an electron transporting layer (ETL). The active layer solution was prepared in o-xylene (the weight ratio of donor material:acceptor material is 1:1~2). The concentration of the donor material was 20 mg/mL. The acceptor material includes the aforementioned near-infrared light organic small molecule with vinyl groups. To completely dissolve the active layer material, the active layer solution is stirred on a hot plate at 100 °C for at least 3 hours. After cooling down to room temperature, filter with PTFE filter membrane (pore size 0.45~1.2 μm), and then heat the active layer solution for 1 hour. Then, the active layer solution is returned to the room temperature for spin coating, and the spin rate was used to control the film thickness in the range of 100~200 nm. Finally, the thin film formed by the coated active layer is annealed at 100 °C for 5 minutes, and then transferred to a thermal evaporation machine. A thin layer (8 nm) of $MoO_3$ is deposited as a hole transporting layer under a vacuum of $3\times10^{-6}$ Torr. In this experiment, a Keithley™ 2400 source meter was used to record the dark current ($J_d$, at a bias of −0.5 V) in the absence of light. External quantum efficiency system was used to measure external quantum efficiency (EQE) with a range of 300~1100 nm (bias voltage 0~−0.5 V), and silicon (300~1100 nm) is used for light source calibration.

It should be noted here that, in practical applications, the first electrode preferably has good light transmittance. The first electrode is usually made of a transparent conductive material, preferably selected from one of the following conductive material groups: indium oxide, tin oxide, halogen-doped tin oxide derivative (Florine Doped Tin Oxide, FTO), or composite metal oxides such as indium tin oxide (ITO) and indium zinc oxide (IZO). The material of the second electrode is a conductive metal, preferably silver or aluminum, more preferably silver. Suitable and preferred materials for ETL include, but are not limited to, metal oxides such as $ZnO_x$, aluminum doped ZnO (AZO), $TiO_x$ or nanoparticles thereof, salts (such as LiF, NaF, CsF or $CsCO_3$), amines (such as primary amines, secondary or tertiary amines), conjugated polymer electrolytes (such as polyethyleneimine), conjugated polymers (such as poly[3-(6-trimethylammoniumhexyl)thiophene], poly(9,9)-bis(2-ethylhexyl-fluorene)-b-poly[3-(6-trimethylammoniumhexyl)thiophen e] or poly[(9,9-bis(3'-(N,N-dimethylamino))propyl)-2,7-fluorene)-alt-2,7-(9,9-dioctylfluorene)], and organic compounds such as tris(8-quinolinyl)-aluminum(III) ($Alq_3$), 4,7-diphenyl-1,10-phenanthroline), or a combination of one or more of the foregoing. Suitable and preferred materials for HTL include, but are not limited to metal oxides such as ZTO, $MoO_x$, $WO_x$, $NiO_x$ or nanoparticles thereof, conjugated polymer electrolytes such as PEDOT:PSS, polymeric acids such as polyacrylates, conjugated polymers such as polytriarylamine (PTAA), insulating polymers such as nafion films, polyethyleneimine or polystyrene sulfonates, organic compounds such as N,N'-diphenyl-N,N'-bis(1-naphthyl)(1,1'-biphenyl)-4,4'-diamine (NPB), N,N'-diphenyl-N,N'-(3-methylbenzene base)-1,1'-biphenyl-4,4'-diamine (TPD), or a combination of one or more of the above.

Please refer to FIG. 12 and Table 4. FIG. 12 shows the test results of dark current and detectivity of comparative example 2, example 1 and example 2 of the active layer material of the present invention. Table 4 shows the test data results of FIG. 12.

TABLE 4

| The test data results of FIG. 12 | | | | |
|---|---|---|---|---|
| | At −0.5 V bias | | | |
| Active layer material | $J_d$ (A/cm$^2$) | D* (Jones) @900 nm | D* (Jones) @940 nm | D* (Jones) @1000 nm |
| comparative example 2 | $5.18\times10^{-9}$ | $8.74\times10^{12}$ | $8.61\times10^{12}$ | $7.13\times10^{12}$ |
| example 1 | $3.44\times10^{-9}$ | $8.84\times10^{12}$ | $8.41\times10^{12}$ | $5.56\times10^{12}$ |
| example 2 | $1.57\times10^{-9}$ | $1.33\times10^{13}$ | $1.27\times10^{13}$ | $7.75\times10^{12}$ |
| | At −2 V bias | | | |
| reference example 1 | $7\times10^{-9}$ | $9.96\times10^{12}$ | $9.60\times10^{12}$ | $6.81\times10^{12}$ |

From the results of the film surface quality test in FIG. 6 to FIG. 11, the combinations capable of forming a good film surface were selected for testing the organic photodetector devices. As shown in FIG. 12 and Table 4, in terms of dark current performance, the dark current of example 2 (acceptor material is mixture A2) is $1.57\times10^{-9}$ A/$cm^2$ which is the lowest dark current. The dark current of example 1 (acceptor material is A2) is $3.44\times10^{-9}$ A/$cm^2$. The dark current of comparative example 2 (acceptor material is A2-2) is $5.18\times10^{-9}$ A/$cm^2$ which is the highest dark current. In example 1, compared with comparative example 2, the carbon chains of $R_1$ and $R_2$ in example 1 are shorter, and the crystallinity is higher than that of the acceptor material A2-2, which can effectively reduce the dark current in terms of device performance. The acceptor material of example 2 is mixture A2, which contains A2-1 with high crystallinity, and after mixing A2-2 and A2, it still exhibits low dark current characteristics. Example 2 is the one with the best film surface performance among the combination containing A2-1. The detectivity of example 1 is $8.84\times10^{12}$, $8.41\times10^{12}$ and $5.56\times10^{12}$ Jones at 900 nm, 940 nm and 1000 nm respectively. Compared with comparative example 2, it has better performance at 900 nm, and slightly worse than comparative example 2 at 940 nm and 1000 nm. Example 2 has the lowest dark current, and its detectivity is $1.33\times10^{13}$, $1.27\times10^{13}$ and $7.75\times10^{12}$ Jones at 900 nm, 940 nm and 1000 nm, respectively. Compared with comparative example 2, there are breakthroughs in 900~1000 nm. From the perspective of the full spectrum, the detectivity of example 2 exceeds $10^{13}$ Jones at 550~980 nm. It is the material with the best performance in the process of non-halogen solvent among small molecules with low energy band gap. Currently the best performing material in the literature is reference example 1 (*Adv. Mater* 2019, 32, 1906027). The dark current is about $7\times10^{-9}$ A/$cm^2$ under −2 V bias, and its detectivity is about $9.96\times10^{12}$, $9.60\times10^{12}$ and $6.81\times10^{12}$ Jones at 900 nm, 940 nm and 1000 nm, respectively. In comparison, example 2 of the present invention still has an advantage in the detectivity at 900-1000 nm.

From the above experimental results, it can be seen that the film surface quality of A2 is better than that of A2-1, and the organic optoelectronic device using A2 as the acceptor material has better device performance than the organic optoelectronic device using A2-2 as the acceptor material. Mixture A2 has a lower dark current because A2-1 helps to reduce the dark current of mixture A2, and thus has a higher detectivity.

In addition, reference example 1 uses a halogen solvent in the manufacturing process. Halogen solvents are not friendly to the environment and cause great harm to the human body, which is a major obstacle in the commercialization of products. The organic optoelectronic device of the present invention uses non-halogen solvents in the manufacturing process, which can effectively reduce the impact of solvents on the environment and human body. Therefore, compared with reference example 1, the commercialization value of the organic optoelectronic device of the present invention is higher.

Please refer to Table 5. Table 5 is a comparative table of yields of each synthesis step.

| | M3 | M5 | M5-1 | M5-2 | M6 | M6-1 | M6-2 | M8 | M8-1 | M8-2 | A2 | A2-1 | A2-2 | Total |
|---|---|---|---|---|---|---|---|---|---|---|---|---|---|---|
| mixture A2 | — | | 74% | | | 93% | | | 96% | | | 71% | | 47.5% |
| A2 | 54% | 74% | — | — | 88% | — | — | 96% | — | — | 58% | — | — | 16.6% |
| A2-1 | — | — | 77% | — | — | 90% | — | — | 92% | — | — | 63% | — | 40.2% |
| A2-2 | — | — | — | 75% | — | — | 88% | — | — | 95% | — | — | 63% | 40.0% |

As shown in Table 5, according to the aforementioned experiments, it is known that A2 can reduce the dark current and improve the detectivity. However, A2 is an asymmetric structure, and it is obviously difficult to increase the yield in synthesis. In order to expand the commercial utilization value of A2, the present invention provides mixture A2, which is synthesized with mixture, and the yield is obviously increased to 47.5%. Moreover, mixture A2 still retains the characteristics of reducing the dark current and improving the detectivity, thereby greatly reducing the cost of mass production.

Based on the above experimental results, the near-infrared light organic small molecule with vinyl groups of the present invention is a non-fullerene acceptor material with an absorption range of 900~1000 nm. The active layer material made of the near-infrared light organic small molecule with vinyl groups of the present invention has a good film surface. The organic optoelectronic device made of this active layer material has the characteristics of low dark current and high detectivity, which are most required by the organic photodetector device in the organic optoelectronic device. In addition, non-halogen solvents are used in the device manufacturing process of the organic optoelectronic device of the present invention to improve environmental friendliness, and still maintain good organic photodetector device performance and device stability performance.

With the detailed description of the above embodiments, it is hoped that the features and spirit of the present invention can be more clearly described, and the scoped of the present invention is not limited by the embodiments disclosed above. On the contrary, the intention is to cover various changes and equivalent arrangements within the scope of the patents to be applied for in the present invention.

What is claimed is:

1. A near-infrared organic small molecule with vinyl groups comprising a structure of formula I:

(formula I)

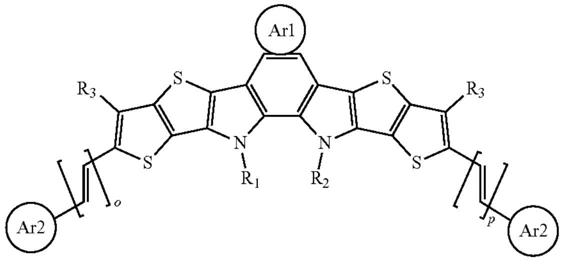

wherein o and p are independently selected from any integer from 0 to 2, and o+p>0;

Arl is an electron-withdrawing group with a unilateral fused ring structure;

Ar2 is a monocyclic or polycyclic structure containing ketone and an electron-withdrawing group, and has a double bond to bond other groups; and $R_1$ is different from $R_2$; $R_1$, $R_2$ and $R_3$ respectively are one of the following groups: C1~C30 alkyl, C1~C30 silyl, C1~C30 alkoxy, C1~C30 alkylthio, C1~C30 haloalkyl, C2~C30 ester, C1~C30 alkylaryl, $C_1$~C30 alkylheteroaryl, $C_1$~C30 silylaryl, $C_1$~C30 silylheteroaryl, $C_1$~C30 alkoxyaryl, $C_1$~C30 alkoxyheteroaryl, $C_1$~C30 alkylthioaryl, $C_1$~C30 alkylthioheteroaryl, $C_1$~C30 haloalkylaryl, $C_1$~C30 haloalkylheteroaryl, C2~C30 ester aryl and C2~C30 ester heteroaryl.

2. The near-infrared organic small molecule with vinyl groups of claim 1, wherein Arl is a five-membered heterocyclic or a six-membered heterocyclic structure having at least one heteroatom, and the heteroatom is independently selected from at least one of S, N, O and Se.

3. The near-infrared organic small molecule with vinyl groups of claim 1, wherein Arl is one of the following structures:

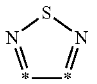 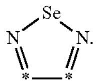

4. The near-infrared organic small molecule with vinyl groups of claim 1, wherein Ar2 further comprises a fused ring structure of at least one of a five-membered ring and a six-membered ring, and the fused ring structure comprises at least one of C═O and cyano.

5. The near-infrared organic small molecule with vinyl groups of claim 4, wherein Ar2 is one of the following structures:

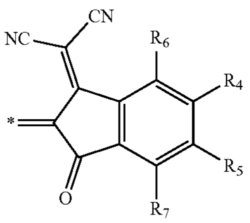

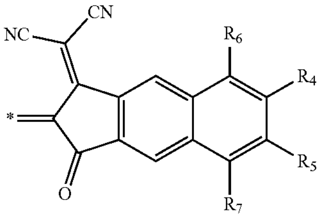

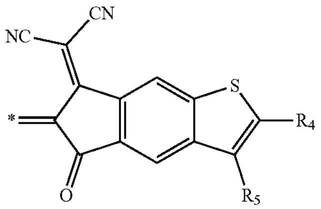

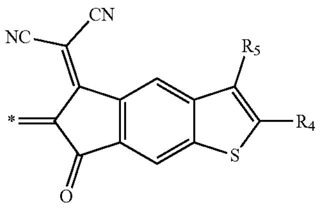

-continued

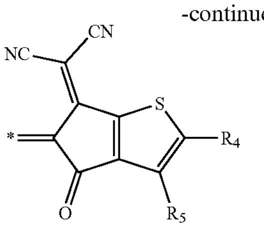

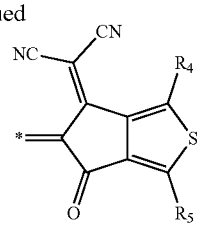

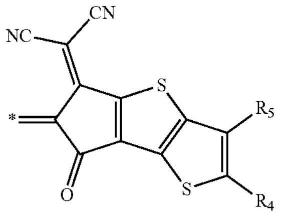

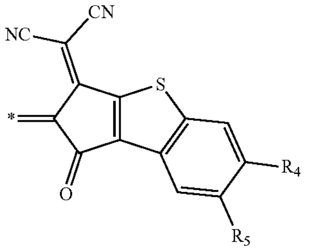

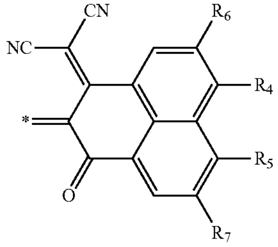

wherein $R_4$, $R_5$, $R_6$ and $R_7$ respectively are one of the following groups: C1~C30 alkyl, C1~C30 silyl, C1~C30 alkoxy, C1~C30 haloalkyl, halogen, cyano and hydrogen.

6. An active layer material comprising:

an acceptor material comprising the near-infrared organic small molecule with vinyl groups of claim 1; and a donor material comprising at least one organic conjugated polymer.

7. The active layer material of claim 6, wherein the acceptor material further comprises at least one of the following structures:

(formula II)

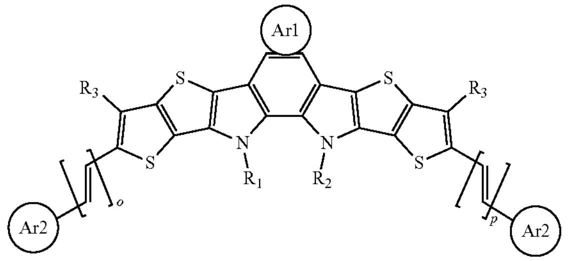

(formula III)

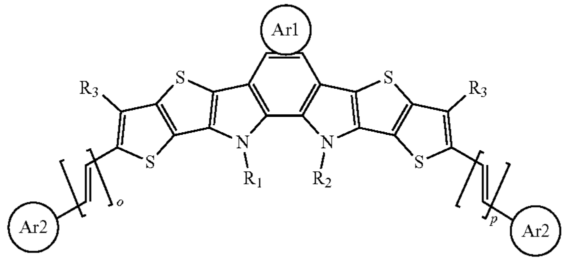

wherein o and p are independently selected from any integer from 0 to 2, and o+p>0;

Ar1 is an electron-withdrawing group with a unilateral fused ring structure;

Ar2 is a monocyclic or polycyclic structure containing ketone and an electron-withdrawing group, and has a double bond to bond other groups; and $R_1$ is different from $R_2$; $R_1$, $R_2$ and $R_3$ respectively are one of the following groups: C1~C30 alkyl, C1~C30 silyl, C1~C30 alkoxy, C1~C30 alkylthio, C1~C30 haloalkyl, C2~C30 ester, C1~C30 alkylaryl, $C_1$~C30 alkylheteroaryl, $C_1$~C30 silylaryl, $C_1$~C30 silylheteroaryl, $C_1$~C30 alkoxyaryl, $C_1$~C30 alkoxyheteroaryl, $C_1$~C30 alkylthioaryl, $C_1$~C30 alkylthioheteroaryl, $C_1$~C30 haloalkylaryl, $C_1$~C30 haloalkylheteroaryl, C2~C30 ester aryl and C2~C30 ester heteroaryl.

8. The active layer material of claim 7, wherein the acceptor material comprises the structures of formula I, formula II and formula III, wherein the molar ratios of the structures of formula I, formula II and formula III are a, b and c respectively, and $0<a\leq 1$, $0<b\leq 1, 0<c\leq 1$, and a+b+c=1.

9. The active layer material of claim 6, wherein the donor material further is one of the following structures:

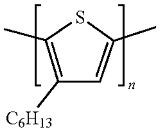
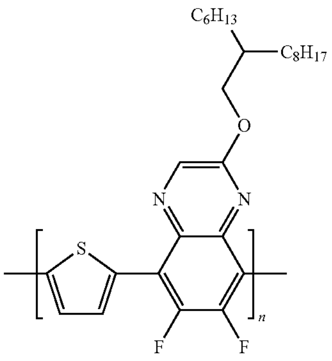
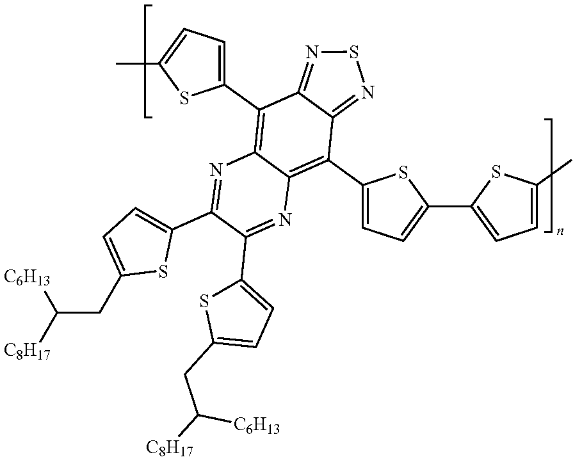
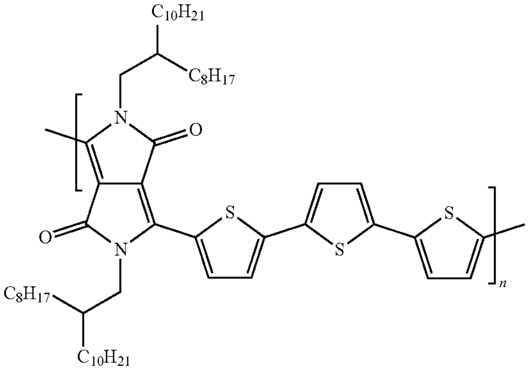
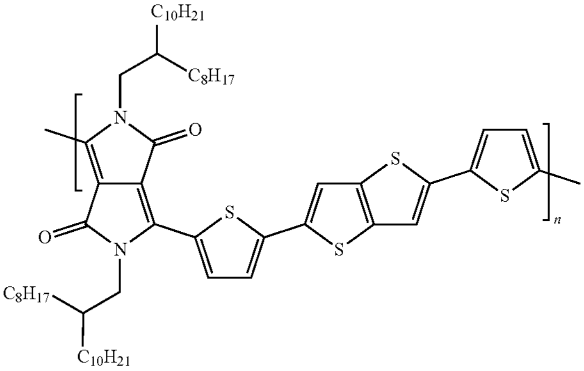
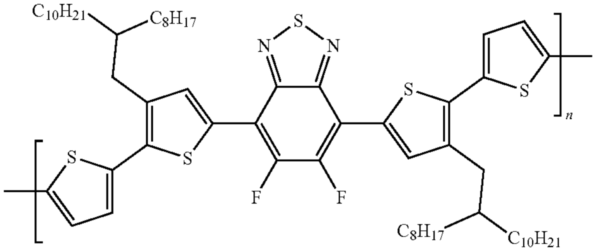
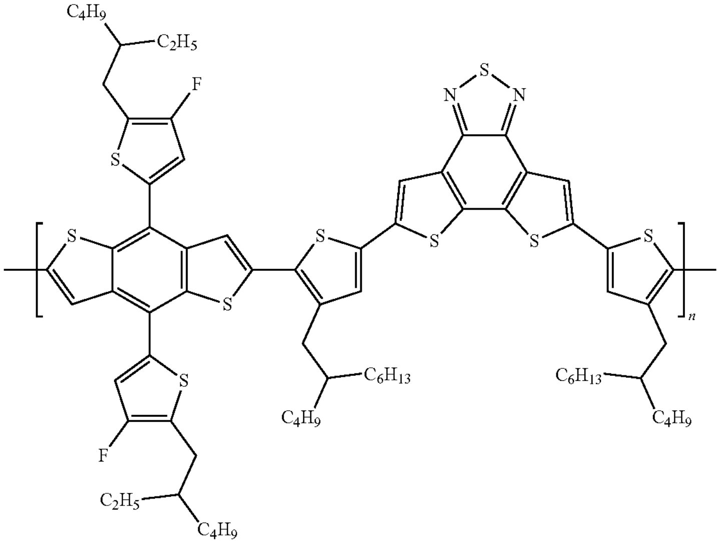

-continued
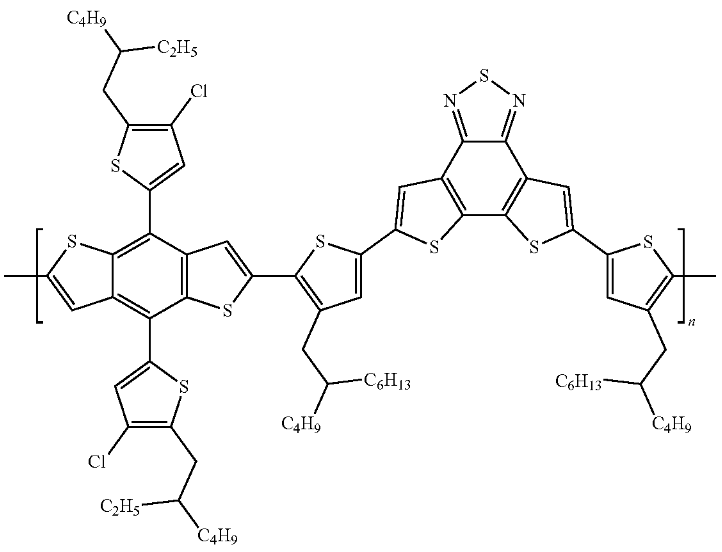
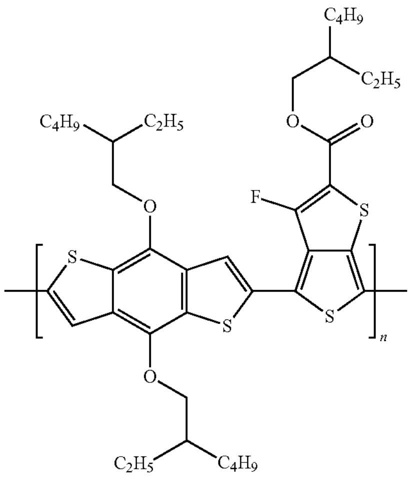
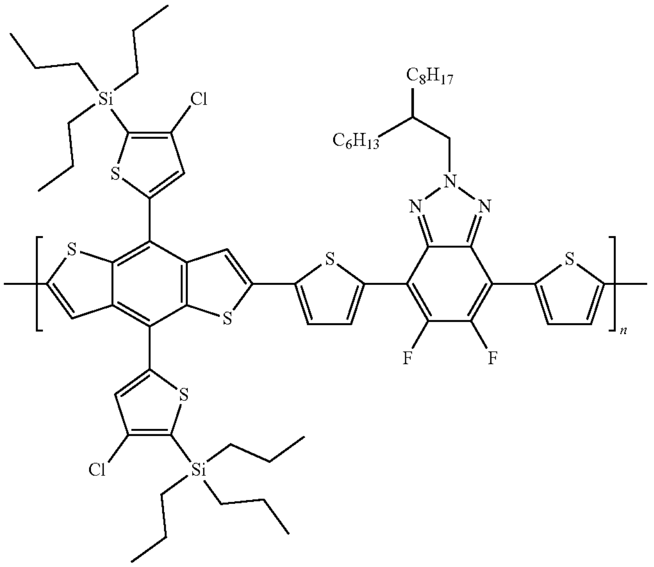
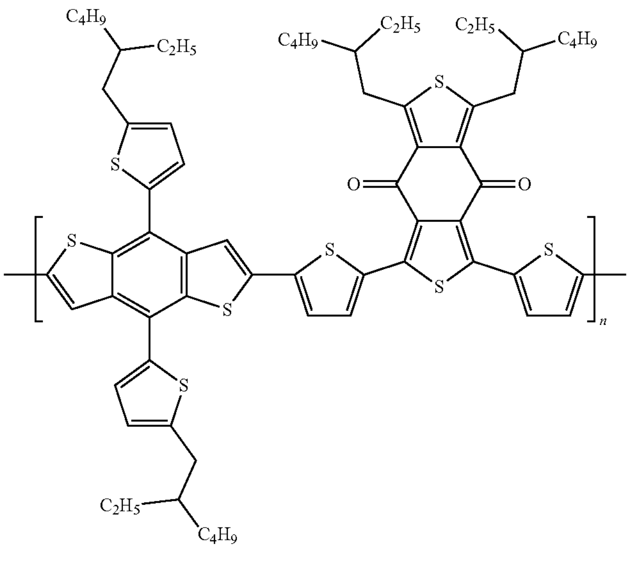

-continued
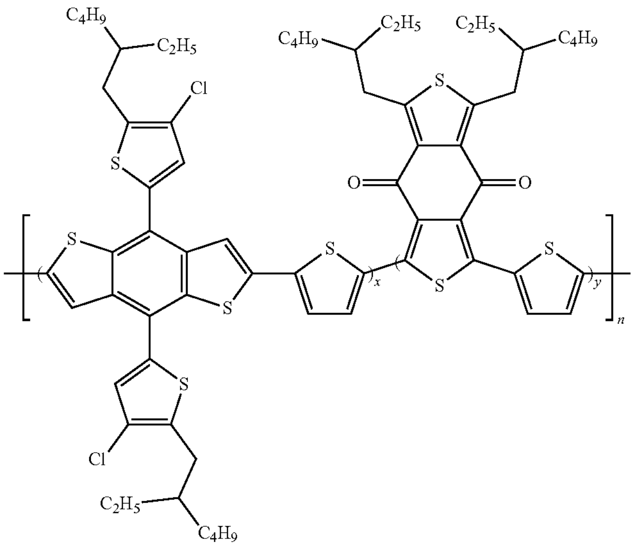
x = y = 0.5
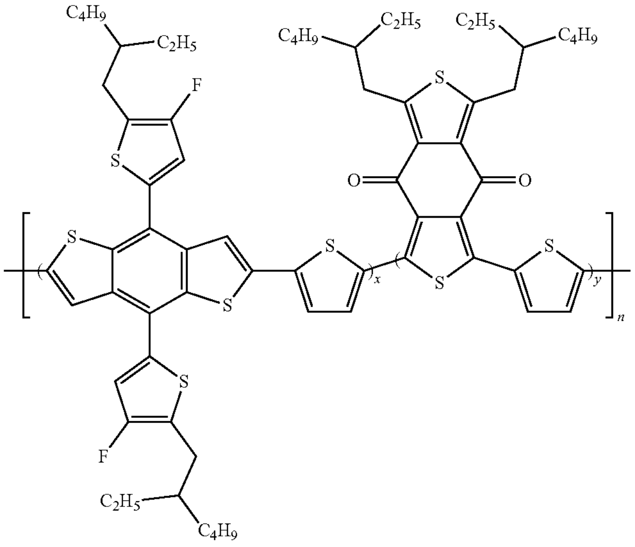
x = y = 0.5
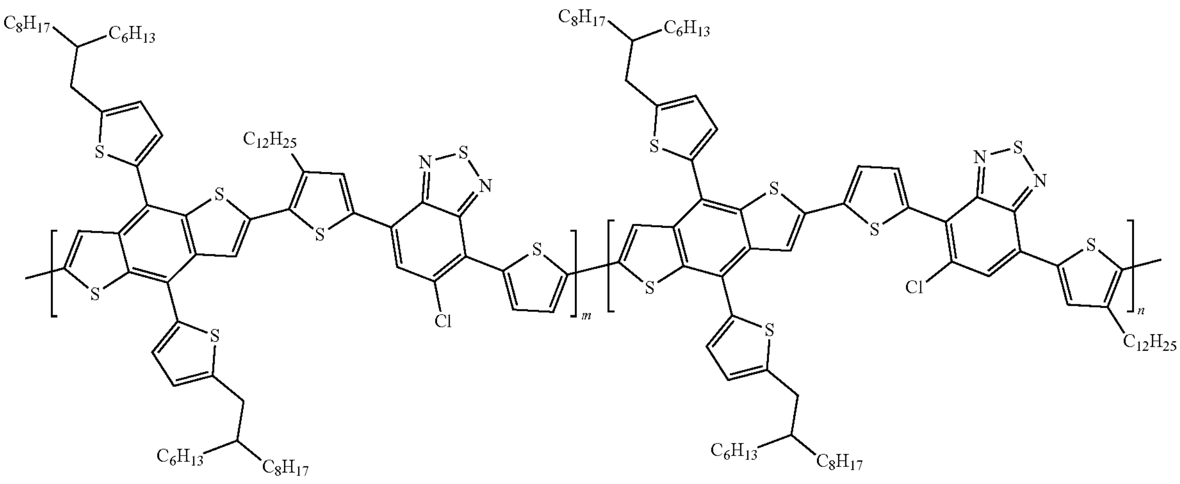

-continued

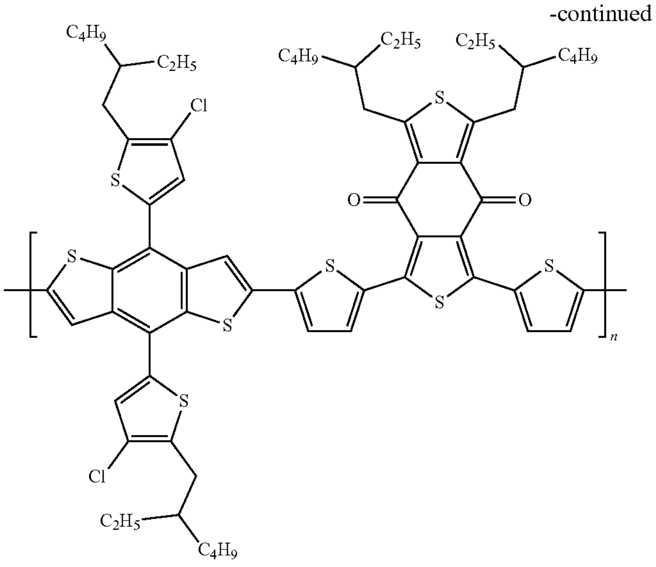

wherein m and n are positive integers.

10. An organic optoelectronic device comprising:

a first electrode;

an active layer comprising an active layer material, and the active layer material at least comprising a near-infrared organic small molecule with vinyl groups of the claim 1; and a second electrode, wherein the active layer is disposed between the first electrode and the second electrode, and at least one of the first electrode and the second electrode is a transparent or semi-transparent electrode.

11. The organic optoelectronic device of claim 10, further comprising a first carrier transporting layer and a second carrier transporting layer, wherein the first carrier transporting layer is disposed between the first electrode and the active layer, the active layer is disposed between the first carrier transporting layer and the second carrier transporting layer, and the second carrier transporting layer is disposed between the active layer and the second electrode.

12. The organic optoelectronic device of claim 10, the active layer material further comprising at least one of the following structures:

(formula II)

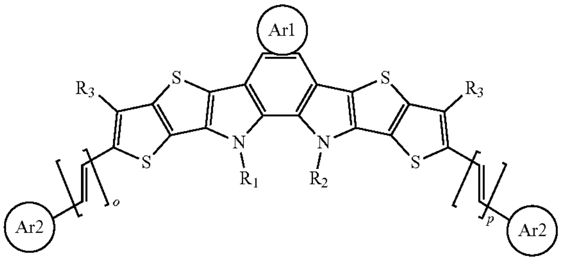

-continued (formula III)

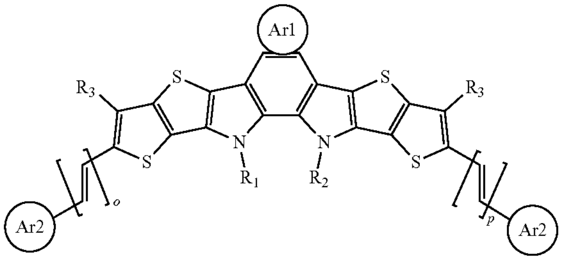

wherein o and p are independently selected from any integer from 0 to 2, and o+p>0;

Arl is an electron-withdrawing group with a unilateral fused ring structure;

Ar2 is a monocyclic or polycyclic structure containing ketone and an electron-withdrawing group, and has a double bond to bond other groups; and $R_1$ is different from $R_2$; $R_1$, $R_2$ and $R_3$ respectively are one of the following groups: C1~C30 alkyl, C1~C30 silyl, C1~C30 alkoxy, C1~C30 alkylthio, C1~C30 haloalkyl, C2~C30 ester, C1~C30 alkylaryl, C1~C30 alkylheteroaryl, C1~C30 silylaryl, C1~C30 silylheteroaryl, $C_1$~C30 alkoxyaryl, $C_1$~C30 alkoxyheteroaryl, C1~C30 alkylthioaryl, C1~C30 alkylthioheteroaryl, $C_1$~C30 haloalkylaryl, $C_1$~C30 haloalkylheteroaryl, C2~C30 ester aryl and C2~C30 ester heteroaryl.

* * * * *